(12) United States Patent
Xiao et al.

(10) Patent No.: US 8,509,893 B2
(45) Date of Patent: Aug. 13, 2013

(54) SUPRAVENTRICULAR STIMULATION TO CONTROL VENTRICULAR RATE

(75) Inventors: Yong-Fu Xiao, Blaine, MN (US); John L. Sommer, Coon Rapids, MN (US); Scott J. Brabec, Elk River, MN (US); Lepeng Zeng, Maple Grove, MN (US); Jon F. Urban, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 248 days.

(21) Appl. No.: 12/913,354

(22) Filed: Oct. 27, 2010

(65) Prior Publication Data

US 2012/0109237 A1    May 3, 2012

(51) Int. Cl.
*A61N 1/372* (2006.01)

(52) U.S. Cl.
USPC ................................. 607/14; 607/9

(58) Field of Classification Search
USPC ............................................. 607/9, 14
See application file for complete search history.

(56) References Cited

U.S. PATENT DOCUMENTS

| | | | |
|---|---|---|---|
| 3,857,399 A | 12/1974 | Zacouto | |
| 3,939,844 A | 2/1976 | Pequignot | |
| 5,213,098 A | 5/1993 | Bennett et al. | |
| 5,411,531 A | 5/1995 | Hill et al. | |
| 5,800,464 A | 9/1998 | Kieval | |
| 6,738,667 B2 | 5/2004 | Deno et al. | |
| 7,024,243 B1 | 4/2006 | Bornzin et al. | |
| 7,096,064 B2 | 8/2006 | Deno et al. | |
| 7,130,684 B2 | 10/2006 | Mulligan et al. | |
| 7,289,850 B2 | 10/2007 | Burnes et al. | |
| 2004/0158292 A1 | 8/2004 | Sheldon et al. | |
| 2008/0077187 A1* | 3/2008 | Levin et al. | 607/9 |
| 2010/0094370 A1 | 4/2010 | Levin et al. | |
| 2010/0198293 A1 | 8/2010 | Kaiser et al. | |
| 2010/0298901 A1 | 11/2010 | Sommer et al. | |

FOREIGN PATENT DOCUMENTS

WO    9725098 A1    7/1997

OTHER PUBLICATIONS

International Search Report and Written Opinion of international application No. PCT/US2011/033981, dated Aug. 2, 2011, 12 pages.
International Preliminary Report on Patentability from international application No. PCT/US2011/033981, dated May 10, 2013, 9 pp.

* cited by examiner

*Primary Examiner* — Joseph Stoklosa
(74) *Attorney, Agent, or Firm* — Reed A. Duthler; Stephen W. Bauer

(57) ABSTRACT

Various techniques for delivering atrial pacing and supraventricular stimulation to achieve a desired ventricular rate and/or cardiac output are described. One example method described includes delivering a pacing signal configured to cause an atrial depolarization to a heart of a patient, wherein the atrial depolarization results in an associated refractory period during the cardiac cycle, and delivering a signal to a supraventricular portion of the heart of the patient subsequent to the atrial refractory period and during a ventricular refractory period of the cardiac cycle.

28 Claims, 21 Drawing Sheets

SUPRAVENTRICULAR STIMULATION TO CONTROL VENTRICULAR RATE

TECHNICAL FIELD

The disclosure relates to medical devices and, more particularly, to medical devices that deliver therapeutic electrical signals to the heart.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient.

Medical leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry such as signal generation and/or sensing circuitry. In some cases, the medical leads and the medical device housing are implantable within the patient. Medical devices with a housing configured for implantation within the patient may be referred to as implantable medical devices.

Implantable cardiac pacemakers or cardioverter-defibrillators, for example, provide therapeutic electrical signals to the heart, e.g., via electrodes carried by one or more implantable medical leads. The therapeutic electrical signals may include pulses for pacing, or shocks for cardioversion or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

SUMMARY

In general, the disclosure is directed toward delivering atrial pacing and supraventricular stimulation to achieve at least one of a desired ventricular rate, stroke volume, cardiac efficiency, cardiac contractility, blood pressure, or cardiac output. Atrial pacing may set the atrial rate to a particular value, e.g., based on the atrial pacing rate. Supraventricular stimulation may decrease the ventricular rate by an amount relative to the atrial pacing rate, e.g., by a percentage of the atrial pacing rate.

In one example, the disclosure is directed to a method comprising delivering a pacing signal configured to cause an atrial depolarization to a heart of a patient, wherein the atrial depolarization results in an associated refractory period during the cardiac cycle, and delivering a signal to a supraventricular portion of the heart of the patient subsequent to the atrial refractory period and during a ventricular refractory period of the cardiac cycle.

In another example, the disclosure is directed to a system comprising a signal generator configured to deliver a pacing signal configured to cause an atrial depolarization to a heart of a patient, wherein the atrial depolarization results in an associated refractory period during the cardiac cycle, and deliver a signal to a supraventricular portion of the heart of the patient subsequent to the atrial refractory period and during a ventricular refractory period of the cardiac cycle and a processor configured to control the signal generator to deliver the pacing signal and the signal to the supraventricular portion of the heart.

In another example, the disclosure is directed to a computer-readable storage medium comprising instructions. When executed, the instructions cause a programmable processor to deliver a pacing signal configured to cause an atrial depolarization to a heart of a patient, wherein the atrial depolarization results in an associated refractory period during the cardiac cycle, and deliver a signal to a supraventricular portion of the heart of the patient subsequent to the atrial refractory period and during a ventricular refractory period of the cardiac cycle.

In another example, the disclosure is directed to a system comprising means for delivering a pacing signal configured to cause an atrial depolarization to a heart of a patient, wherein the atrial depolarization results in an associated refractory period during the cardiac cycle, and means for delivering a signal to a supraventricular portion of the heart of the patient subsequent to the atrial refractory period and during a ventricular refractory period of the cardiac cycle.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
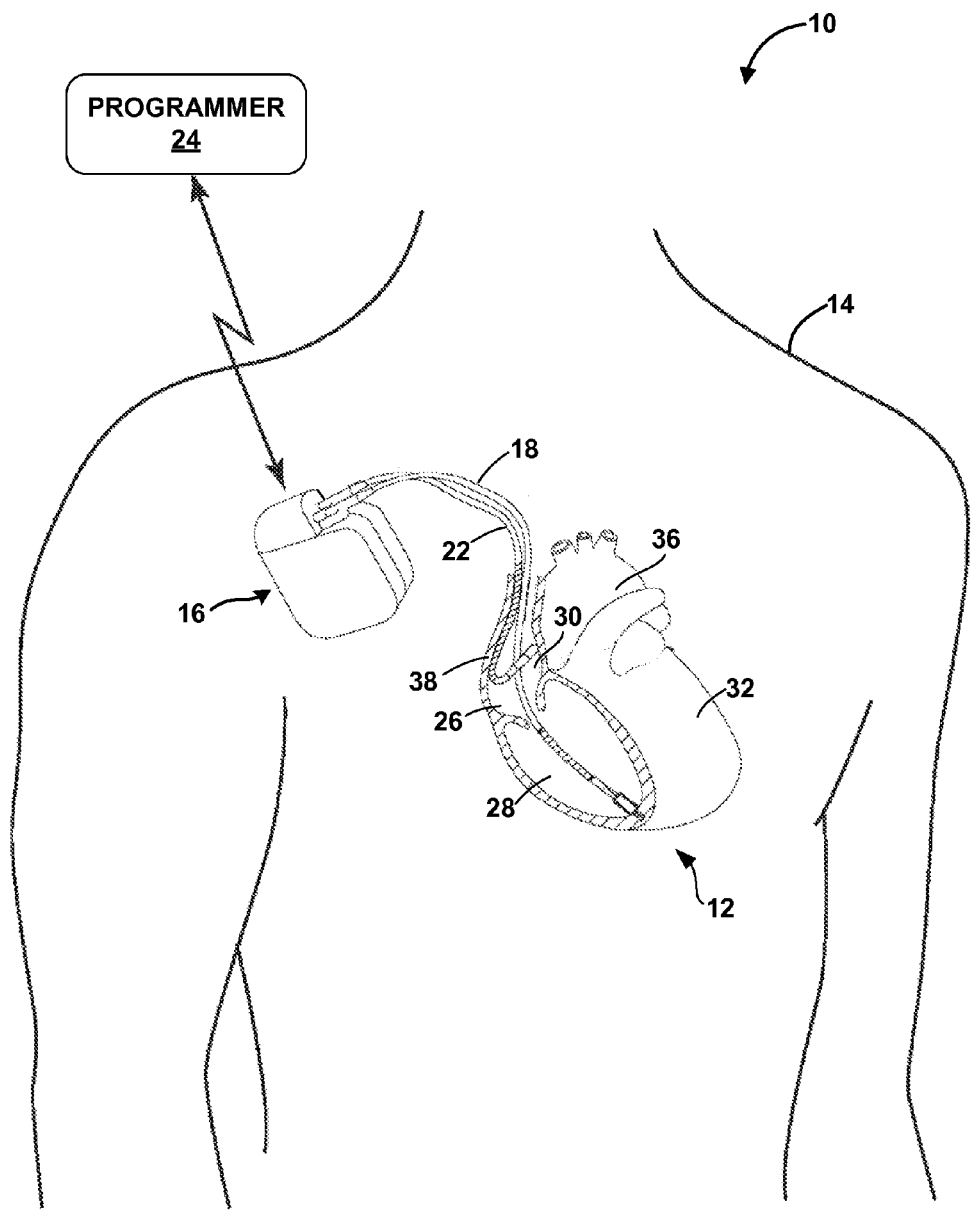
FIG. 1 is a conceptual diagram illustrating an example system comprising an implantable medical device (IMD) coupled to a plurality of leads that may be used to monitor one or more physiological parameters of a patient and/or provide therapy to the heart of a patient.

In a healthy heart, the sino-atrial node (SAN), also referred to as the sinus node, initiates action potentials which propagate through the whole heart via a conductive system of the heart. Compared with the ventricles, the SAN, atria, and atrioventricular node (AVN) are normally excited earlier and recover earlier in the cardiac cycle. Additionally, due to longer action potential durations associated with the ventricular myocardium, the refractory period of the ventricles continues after the end of the atrial and nodal refractory periods. Therefore, there is a stimulus time window in which the atria, SAN, and/or AVN may be excited while the ventricles remain refractory to stimulation.

Excitation of the atria, SAN, and/or AVN during the ventricular refractory period, referred to in this disclosure as cardiac electrical-window therapy (CEWT), may reset the atrial cycle, e.g., reset the SAN, and start a new refractory period in the atrial and AV nodal tissue, without triggering a ventricular contraction. The new atrial refractory period may delay ventricular contraction until a subsequent atrial depolarization capable of propagating to and depolarizing the non-refractory ventricles, thereby increasing the period of time between ventricular contractions. Thus, the ventricular rate may be reduced by up to fifty percent from the SAN rate. Experimental data has shown that in conjunction with this reduction in ventricular rate, both the systolic and diastolic blood pressures may be reduced. The degree of reduction in ventricular rate and blood pressure may vary with the timing of the CEWT, e.g., delivered to the atria, SAN, and/or AVN, relative to the preceding atrial and/or ventricular depolarizations. Thus, the effect of CEWT may be titrated against a desired ventricular rate and/or blood pressure, or reduction in ventricular rate and/or blood pressure. Additionally, as described in this disclosure, atrial pacing may be used in combination with CEWT to aid in achieving at least one of a target ventricular rate, stroke volume, cardiac efficiency, cardiac contractility, blood pressure, or cardiac output.

When delivered without accompanying atrial pacing, CEWT may decrease the ventricular rate relative to an intrinsic atrial rate. However, decreasing ventricular rate by a percentage within the range allowed by CEWT may not result in a desired ventricular rate, e.g., may result in a ventricular rate that is too slow. Delivering atrial pacing may allow CEWT to decrease the ventricular rate relative to the atrial pacing rate, e.g., within a percentage range allowed by CEWT. The atrial pacing rate may be selected based on the target ventricular rate. Thus, atrial pacing may pace the atria at a relatively high rate, and CEWT may modify the ventricular rate to a desirable level beneficial to the patient.

CEWT may be delivered using stimulation parameters of typical cardiac pacing pulses or pulse bursts having burst envelopes corresponding to the duration and/or morphology of normal cardiac pacing pulses. For example, CEWT may be delivered using an amplitude in the range of approximately 1 volt to approximately 2 volts and a pulse width of approximately 0.5 ms to approximately 1 ms. Longer pulse durations, e.g. 10 milliseconds (ms) or more or a train of pulses may also be employed. The particular form of the pulse is not critical so long as it triggers a depolarization of the desired atrial or nodal tissue. Proper timing of the CEWT pulses within the defined excitation window may be important to assure that the desired effect is produced without induction of arrhythmias.

The time window for delivery of a CEWT stimulus extends from the point within a cardiac cycle at which the atrial or nodal tissue to be stimulated becomes non-refractory up to the point within the cardiac cycle at which the stimulated atrial or nodal depolarization could propagate to the ventricles to cause a ventricular depolarization. The time window may vary from patient to patient, but generally falls between the end of the atrial and/or nodal refractory periods and the end of the ventricular refractory period. Thus, the window generally extends within a time period occurring between about 80 ms to about 200 ms following a normally conducted ventricular depolarization. The timing and durations of refractory periods may vary with the individual and with the underlying heart rhythm. Thus, the duration of the time window may also vary. Timing of the CEWT pulses may be based upon a preceding atrial depolarization, a preceding ventricular depolarization, or possibly both. Timing of the CEWT pulses may be predefined by the attending physician and programmed into the device or may be varied by the device in order to achieve a desired ventricular rate, stroke volume, cardiac efficiency, cardiac contractility, blood pressure, or cardiac output.

FIG. 1 is a conceptual diagram illustrating an example system 10 that may be used to monitor one or more physiological parameters of patient 14 and/or to provide therapy, e.g., atrial pacing and cardiac electrical-window therapy (CEWT), to heart 12 of patient 14. System 10 includes an implantable medical device (IMD) 16, which is coupled to leads 18 and 22, and programmer 24. IMD 16 may be an implantable pacemaker that provides electrical signals to heart 12 via electrodes coupled to one or more of leads 18 and 22. In addition to pacing therapy, IMD 16 may deliver CEWT, e.g., proximate to the SAN, AVN, or to other supraventricular tissue. In some examples, IMD 16 may also include cardioversion and/or defibrillation functionalities. Patient 14 is ordinarily, but not necessarily, a human patient.

Leads 18 and 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. RV lead 18 may be used to sense electrical activity within right ventricle 28 and/or deliver RV pacing or other therapies to heart 12.

In the example shown in FIG. 1, right atrial (RA) lead 22 extends through one or more veins and the vena cava, and into the right atrium 26 of heart 12. RA lead 22 may be used to sense electrical activity within right atrium 26, pace right atrium 26, and deliver CEWT to right atrium 26, e.g., to AVN 30 or proximate to AVN 30. In some examples, the distal end of lead 22 may be located in or near AVN 30 or in or near right atrial appendage (RAA) 38, e.g., to help facilitate atrial pacing and CEWT. As described in further detail below, in some examples, two leads may be implanted within right atrium 26. For example, one lead may deliver atrial pacing signals, e.g., to RAA 38 or proximate to RAA 38, and the other lead may deliver CEWT, e.g., to AVN 30 or proximate to AVN 30.

In some examples, system 10 may additionally or alternatively include one or more leads or lead segments (not shown in FIG. 1) that deploy one or more electrodes within left atrium 36, left ventricle 32, the vena cava or other vein, or within or near the aorta. These electrodes may allow alternative electrical sensing and/or stimulation configurations that may provide improved or supplemental sensing and/or stimulation in some patients. Furthermore, in some examples, system 10 may include temporary or permanent epicardial or subcutaneous leads, instead of or in addition to leads 18 and 22. Such leads may be used for one or more of cardiac sensing, pacing, CEWT, or cardioversion/defibrillation.

IMD 16 may sense electrical signals attendant to the depolarization and repolarization of heart 12 via electrodes (not shown in FIG. 1) coupled to at least one of the leads 18 and 22. In some examples, IMD 16 provides pacing pulses and CEWT to heart 12 based on the electrical signals sensed within heart 12. The configurations of electrodes used by IMD 16 for sensing and pacing may be unipolar or bipolar. IMD 16 may detect arrhythmia of heart 12, such as flutter, tachycardia, or fibrillation of atria 26 and 36 and/or ventricles 28 and 32. In some examples, IMD 16 provides pacing pulses and CEWT to heart 12 based on a detected arrhythmia. IMD 16 may also provide defibrillation therapy and/or cardioversion therapy via electrodes located on at least one of leads 18 and 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

System 10 may also sense blood pressure, e.g., systolic and/or diastolic pressures. In some examples, one or both of leads 18 and 22 may include a pressure sensor (not shown). In other examples, system 10 may include one or more other pressure sensors, e.g., wirelessly coupled to IMD 16 or coupled to IMD 16 via additional leads. In some examples, one or more electrodes of leads 18 and 22 may also be utilized to measure impedance, e.g., to determine volumetric measurements of the expansion and contraction of right atrium 26 and/or right ventricle 28. In some examples, electrodes on additional leads placed into or proximate to left atrium 36 and/or left ventricle 32 may be utilized to measure impedance, e.g., to determine volumetric measurements of the expansion and contraction of left atrium 36 and/or left ventricle 32.

Programmer 24 may be a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18 and 22, or a power source of IMD 16. As another example, the user may interact with programmer 24 to program, e.g., select parameters for, therapies provided by IMD 16, such pacing and CEWT and, optionally, cardioversion and/or defibrillation. The user may also interact with programmer 24 to retrieve information regarding atrial pacing, CEWT, stimulus time windows associated with CEWT, and reductions in ventricular rate or other physiological parameters.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the implant site of IMD 16 in order to improve the quality or security of communication between IMD 16 and programmer 24.

Figure 2:
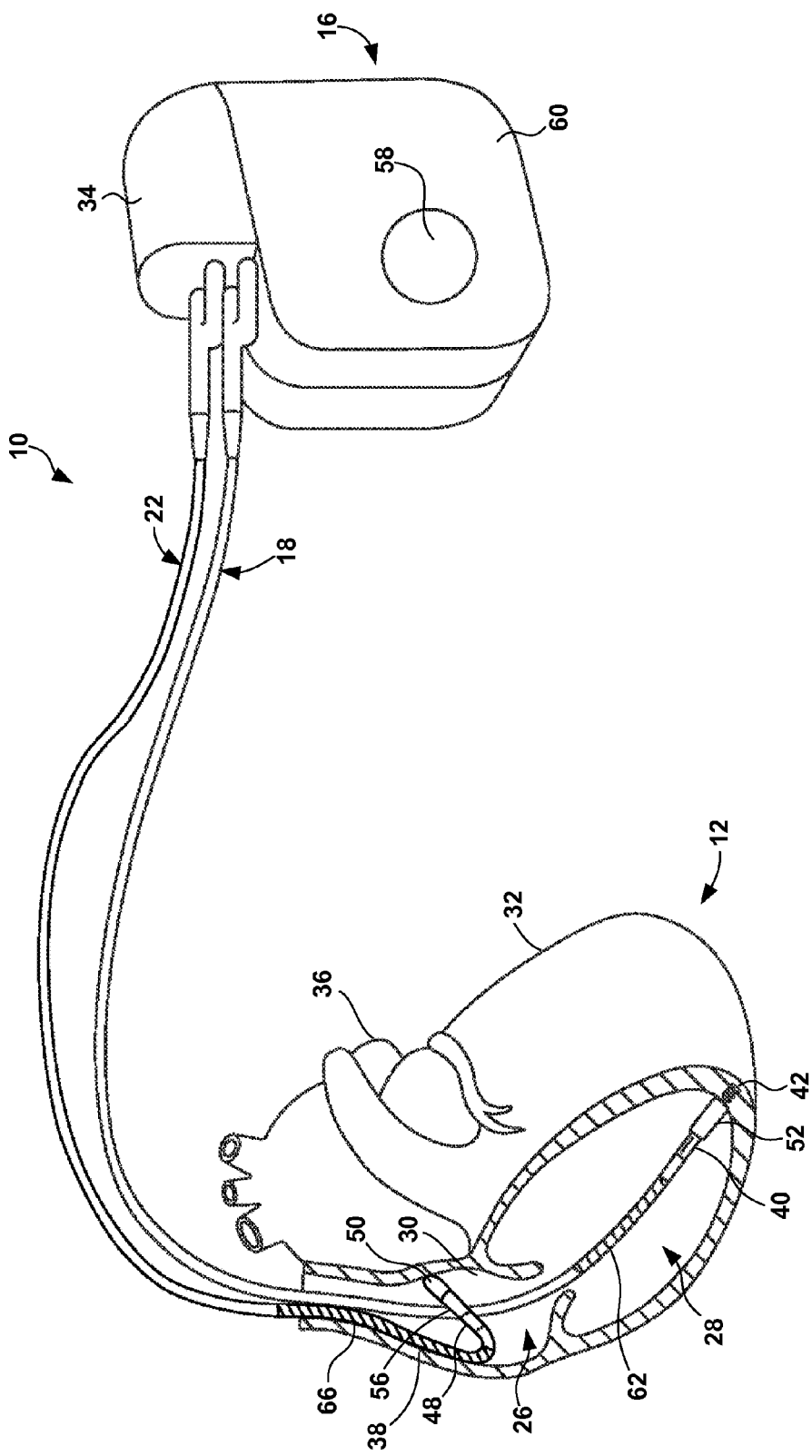
FIG. 2 is a conceptual diagram further illustrating the IMD and leads of the system of FIG. 1 in conjunction with the heart.

FIG. 2 is a conceptual diagram illustrating IMD 16 and leads 18 and 22 of system 10 in greater detail. Leads 18 and 22 may be electrically coupled to a signal generator and a sensing module of IMD 16 via connector block 34. In some examples, proximal ends of leads 18 and 22 may include electrical contacts that electrically couple to respective electrical contacts within connector block 34 of IMD 16. In some examples, a single connector, e.g., an IS-4 or DF-4 connector, may connect multiple electrical contacts to connector block 34. In addition, in some examples, leads 18 and 22 may be mechanically coupled to connector block 34 with the aid of set screws, connection pins, snap connectors, or another suitable mechanical coupling mechanism.

Each of the leads 18 and 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 48 and 50 are located proximate to a distal end of lead 22. In the illustrated example, there are no electrodes located in left atrium 36 or left ventricle 32. However, other examples may include electrodes in left atrium 36 and/or left ventricle 32.

Electrodes 40 and 48 may take the form of ring electrodes, and electrodes 42 and 50 may take the form of extendable helix tip electrodes mounted retractably within insulative electrode heads 52 and 56, respectively. In some examples, one or more of electrodes 42 and 50 may take the form of pre-exposed helix tip electrodes. In other examples, one or more of electrodes 42 and 50 may take the form of small circular electrodes at the tip of a tined lead or other fixation element. Leads 18 and 22 also include elongated electrodes 62 and 66, respectively, which may take the form of a coil. Each of the electrodes 40, 42, 48, 50, 62, and 66 may be electrically coupled to a respective one of the coiled conductors within the lead body of its associated lead 18 and 22, and thereby coupled to respective ones of the electrical contacts on the proximal end of leads 18 and 22.

Helix tip electrode 50, which may be extendable or pre-exposed, of RA lead 22 may be inserted into the tissue of right atrium 26 to substantially fix RA lead 22 within right atrium 26. In the example illustrated in FIG. 2, helix tip electrode 50 is inserted into or proximate to the endocardium of the septum that separates right atrium 26 and left atrium 36 at a inferior portion of right atrium 26, e.g., within or proximate to the region of AVN 30, to deliver CEWT. In the illustrated example, electrode 48 is positioned proximate to RAA 38, e.g., to deliver pacing signals to right atrium 26. In other examples, helix tip electrode 50 may be inserted into or proximate to RAA 38, e.g., to deliver pacing signals to right atrium 26, and electrode 48 may be positioned within or proximate to AVN 30, e.g. to deliver CEWT. In some examples, IMD 16 may deliver pacing signals and CEWT to the same location, e.g., via bipolar electrode pair 48 and 50. As described previously, RA lead 22 may be positioned such that RA lead 22 may sense electrical activity within right atrium 26, pace right atrium 26, and also deliver CEWT, e.g., to or proximate to AVN 30. Helix tip electrode 50 may aid in maintaining the distal portion of RA lead 22 in the appropriate position to provide such functionality. Lead 22 may also include other fixation mechanisms, e.g., to maintain electrode 48 in an appropriate position.

Additionally, IMD 16 is not limited to delivering pacing pulses proximate to RAA 38 and/or CEWT to or proximate to AVN 30. IMD 16 may deliver pacing pulses to any portion in or proximate to right atrium 26 capable of initiating depolarization and contraction in right atrium 26. In general, IMD 16 may deliver CEWT to any supraventricular portion of heart 12, such as to or proximate to the SAN, right atrium 26, and/or AVN 30.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and CEWT signals, as well as a sensing module for monitoring the rhythm of heart 12.

IMD 16 may sense electrical signals attendant to the depolarization and repolarization of heart 12 via electrodes 40, 42, 48, 50, 58, 62, and 66. The electrical signals are conducted to IMD 16 from the electrodes via the respective leads 18 and 22 or, in the case of housing electrode 58, a conductor coupled to housing electrode 58. IMD 16 may sense such electrical signals via any bipolar combination of electrodes 40, 42, 48, 50, 58, 62, and 66. Furthermore, any of the electrodes 40, 42, 48, 50, 58, 62, and 66 may be used for unipolar sensing in combination with housing electrode 58.

System 10 may also sense blood pressure, e.g., systolic and/or diastolic pressures. In some examples, one or both of leads 18 and 22 may include a pressure sensor (not shown). In other examples, system 10 may include one or more other pressure sensors, e.g., wirelessly coupled to IMD 16 or coupled to IMD 16 via additional leads. For example, a separately housed pressure sensor positioned in the pulmonary artery of patient 14 may wirelessly communicate blood pressure data with IMD 16. In some examples, one or more of electrodes 40, 42, 48, 50, 58, 62, and 66 may also be utilized to measure impedance, e.g., to determine volumetric measurements of the expansion and contraction of right atrium 26 and/or right ventricle 28. In some examples, electrodes on additional leads placed into left atrium 36 and/or left ventricle 32 may be utilized to measure impedance, e.g., to determine volumetric measurements of the expansion and contraction of left atrium 36 and/or left ventricle 32.

In some examples, IMD 16 delivers pacing pulses via bipolar combinations of electrodes 40, 42, 48, 50, 62, and 66 to produce depolarization of cardiac tissue of heart 12. In some examples, IMD 16 delivers pacing pulses via any of electrodes 40, 42, 48, 50, 62, and 66 in combination with housing electrode 58 in a unipolar configuration. For example, IMD 16 may deliver pacing signals to right atrium 26 via any unipolar or bipolar combination of electrodes 48, 50, 58, and 66.

IMD 16 may deliver CEWT via electrodes 48 and 50 of RA lead 22, e.g., in a bipolar configuration, or in a unipolar configuration in combination with housing electrode 58 or electrode 66 of RA lead 22. IMD 16 may deliver CEWT during a stimulus time window in which the SAN, atria 26 and 36, and/or AVN 30 may be excited while ventricles 28 and 32 remain refractory to stimulation. As described in this disclosure, IMD 16 may deliver CEWT in conjunction with atrial pacing. For example, IMD 16 may deliver a pacing signal, which may take the form of one or more pulses or other signals, to right atrium 26 via any unipolar or bipolar combination of electrodes 48, 50, 58, and 66. Subsequent to the pacing signal, IMD 16 may deliver CEWT via electrodes 48, 50, and/or 66 during a stimulus time window in which the SAN, atria 26 and 36, and/or AVN 30 may be excited while ventricles 28 and 32 remain refractory to stimulation.

The stimulus time window may be based on the timing of the paced atrial depolarization and/or a normally conducted ventricular depolarization subsequent to paced atrial depolarization. A normally conducted ventricular depolarization may be a ventricular depolarization preceded by an atrial depolarization at an interval corresponding to a normal A-V conduction interval, i.e., not a premature ventricular depolarization. The ventricular depolarization may be sensed, paced or some combination of both, e.g., during delivery of ventricular resynchronization therapy. For example, IMD 16 may detect a normally conducted ventricular depolarization subsequent to the atrial pacing signal and deliver CEWT within a time period occurring between about 80 ms to about 200 ms following a normally conducted ventricular depolarization. As another example, the time window may be based on the timing of the paced atrial depolarization, and IMD 16 may deliver CEWT within a defined time period following the atrial pacing signal. In other examples, the timing of both the paced atrial depolarization and the ventricular depolarization, e.g., paced or sensed, may be employed to determine the CEWT delivery time or the permitted range of delivery times, i.e., the stimulus time window.

The intervals for CEWT may be pre-programmed into IMD 16, e.g., by a physician based upon an electrophysiological study of the patient. Alternatively, IMD 16 may determine a CEWT delivery time by varying the timing of CEWT within a time window and adjusting the defined stimulation intervals to produce a desired result, e.g., using a sensed physiological parameter as feedback for the adjustment of the CEWT delivery time. The desired result may be, for example, a target ventricular rate or blood pressure, or a target reduction in ventricular rate or blood pressure, which may be defined as an absolute reduction or percentage or ratio. Other physiological parameters, such as stroke volume, cardiac efficiency, cardiac contractility, or cardiac output, may also be used as feedback for the adjustment of the CEWT delivery time.

Activation of CEWT may be triggered by IMD 16, for example, in response to a suprathreshold heart rate or blood pressure, and IMD 16 may deactivate CEWT in response to the heart rate or blood pressure returning to acceptable ranges. IMD 16 may determine that the heart rate or blood pressure is excessive by comparing the values of these parameters to pre-defined threshold values, e.g., defined by a user via programmer 24 or another computing device. IMD 16 may additionally or alternatively utilize other physiological parameters, such as stroke volume, cardiac efficiency, cardiac contractility, or cardiac output, to activate CEWT. Alternatively, a user, e.g., a physican or patient 14, may activate and deactivate CEWT via programmer 24.

Furthermore, IMD 16 may deliver defibrillation shocks to heart 12 via any combination of elongated electrodes 62 and 66, and housing electrode 58. Electrodes 58, 62, and/or 66 may also be used to deliver cardioversion shocks to heart 12. Electrodes 62 and 66 may be fabricated from any suitable electrically conductive material, such as, but not limited to, platinum, platinum alloy, or other materials known to be usable in implantable defibrillation electrodes.

The configuration of system 10 illustrated in FIGS. 1 and 2 is merely one example. In other examples, a system may include epicardial leads and/or patch electrodes instead of or in addition to the transvenous leads 18 and 22 illustrated in FIG. 1. Further, IMD 16 need not be implanted within patient 14. In examples in which IMD 16 is not implanted in patient 14, IMD 16 may deliver pacing pulses and CEWT and, optionally, other therapies to heart 12 via percutaneous leads that extend through the skin of patient 14 to a variety of positions within or outside of heart 12.

In addition, in other examples, a system may include any suitable number of leads coupled to IMD 16, and each of the leads may extend to any location within or proximate to heart 12. For example, system 10 may additionally or alternatively include one or more leads or lead segments that deploy one or more electrodes within left atrium 36, left ventricle 32, the vena cava or other vein, or within or near the aorta. These electrodes may allow alternative electrical sensing and/or stimulation configurations that may provide improved or supplemental sensing and/or stimulation in some patients. Other examples of systems may include three transvenous leads, e.g., include two leads located as illustrated in FIGS. 1 and 2 and an additional lead located within or proximate to left atrium 36. An example of this type of system is shown in FIG. 3.

Figure 3:
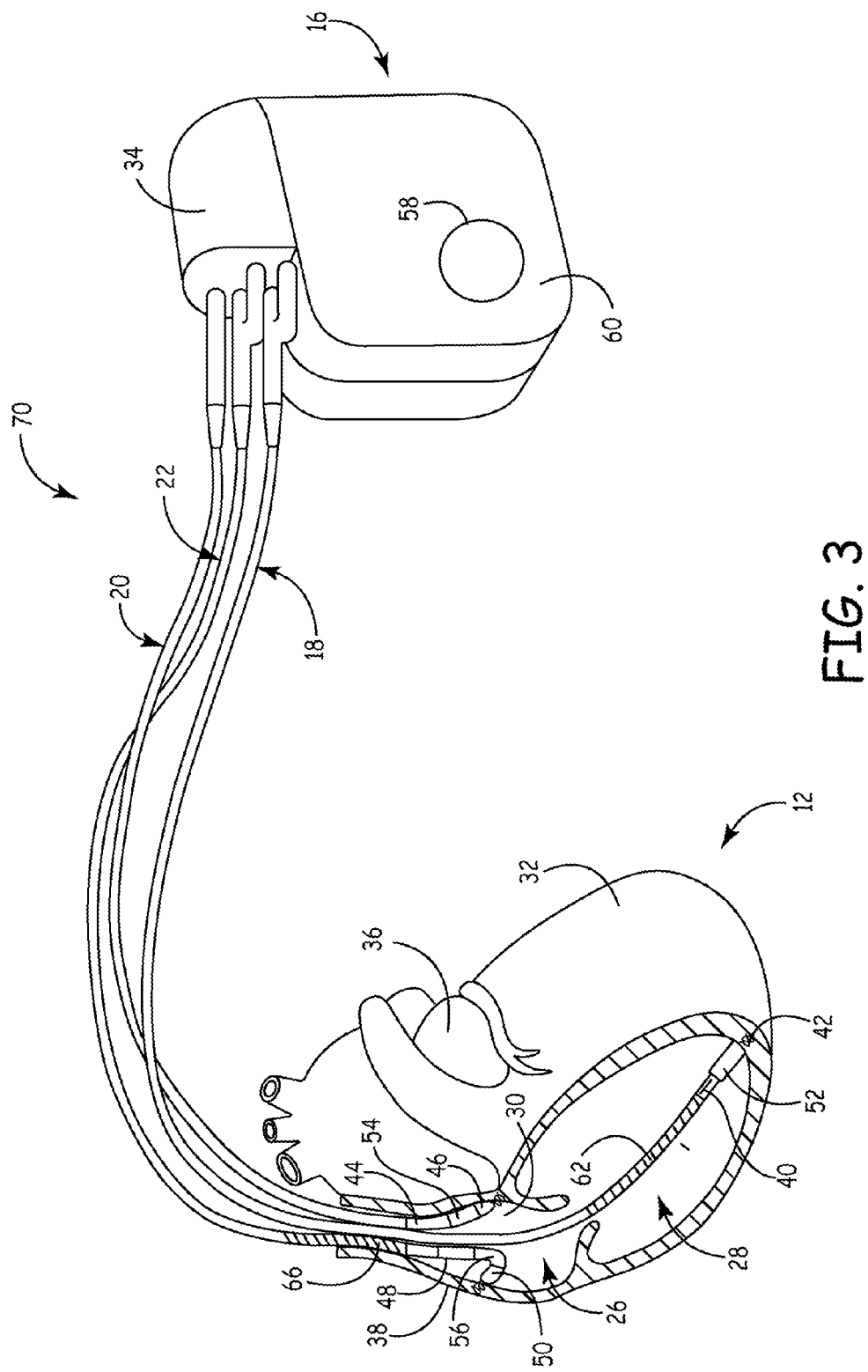
FIG. 3 is a conceptual drawing illustrating the example IMD of FIG. 1 coupled to a different example configuration of three implantable medical leads in conjunction with a heart.

FIG. 3 is a conceptual diagram illustrating another example of a system 70, which is similar to system 10 of FIGS. 1 and 2, but includes a third lead 20 in addition to leads 18 and 22. Like lead 22, lead 20 is implanted within right atrium 26.

In the example of FIG. 3, lead 20 includes bipolar electrodes 44 and 46 located proximate to its distal end. In some examples, lead 20 may also include one or more elongated electrodes to deliver cardioversion, defibrillation, and/or other therapies to heart 12. Electrodes 44 may a ring electrode, and electrodes 46 may be extendable helix tip electrodes mounted retractably within insulative electrode head 54. Each of electrodes 44 and 46 may be electrically coupled to a respective one of the coiled conductors within the lead body of lead 20, and thereby coupled to respective ones of the electrical contacts on the proximal end of lead 20. Electrodes 44 and 46 may sense electrical signals attendant to the depolarization and repolarization of heart 12, e.g., in a bipolar configuration or in a unipolar configuration in combination with housing electrode 58.

In the example of FIG. 3, helix tip electrode 46 of lead 20 is inserted into or proximate to the endocardium of the septum that separates right atrium 26 and left atrium 36 at a inferior portion of right atrium 26, e.g., within or proximate to the region of AVN 30, to deliver CEWT. For example, any unipolar or bipolar combination of electrodes 44, 46, and 58 may be used to deliver CEWT. Whereas, helix tip electrode 50 of lead 22 is inserted into or proximate to RAA 38, e.g., to deliver pacing signals to right atrium 26. For example, any unipolar or bipolar combination of electrodes 48, 50, 58, and 66 may be used to deliver pacing signals to right atrium 26. In this manner, lead 22 may be positioned to deliver atrial pacing signals, e.g., to or proximate to RAA 38, and lead 20 may be positioned to deliver CEWT, e.g., to or proximate to AVN 30. A system 70 that includes two atrial leads 20 and 22 may be desirable if IMD 16 delivers pacing pulses and CEWT to two different locations, e.g., separated by a substantial distance.

Although system 10 is primarily described in this disclosure for purposes of example, this disclosure is applicable to any appropriate system capable of delivering atrial pacing and CEWT.

Figure 4:
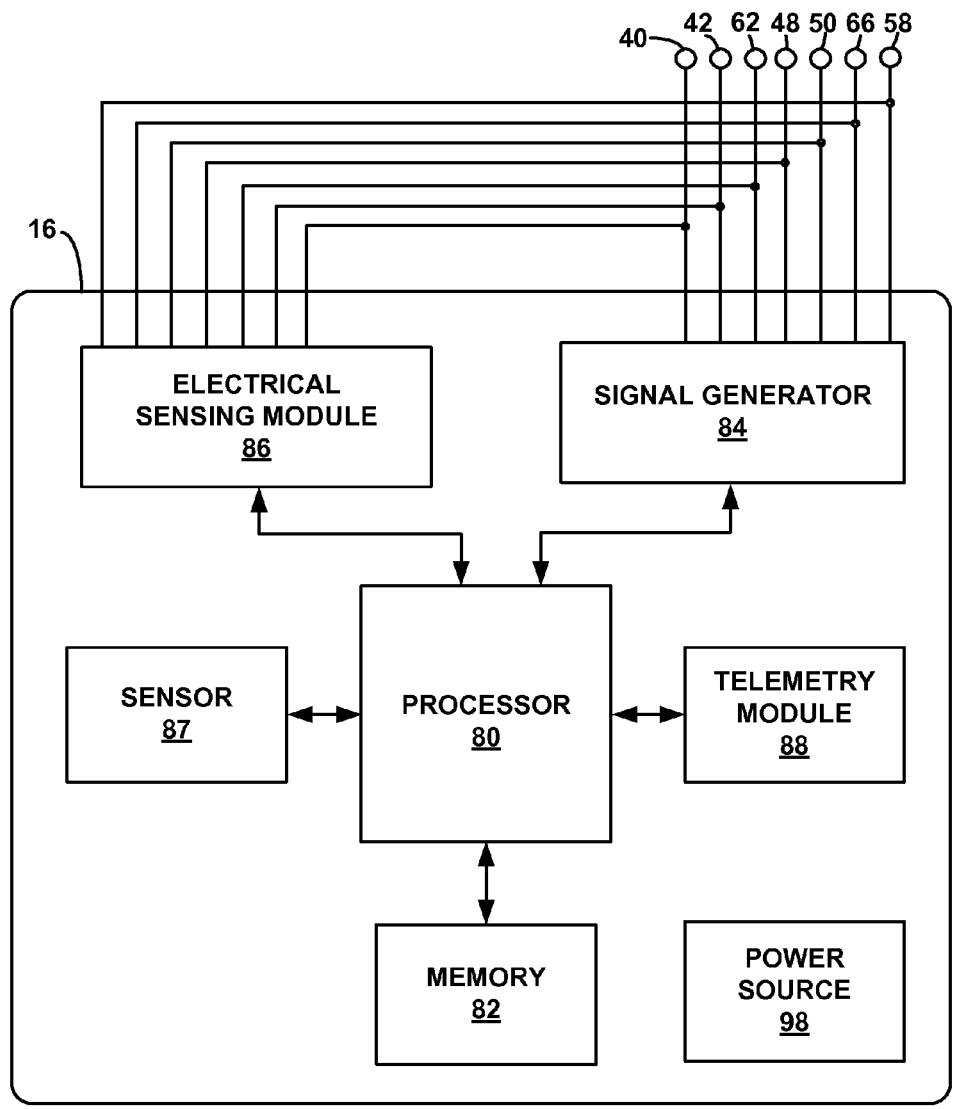
FIG. 4 is a functional block diagram illustrating an example configuration of the IMD of FIG. 1.

FIG. 4 is a functional block diagram illustrating one example configuration of IMD 16. In the example illustrated by FIG. 4, IMD 16 includes a processor 80, memory 82, signal generator 84, electrical sensing module 86, sensor 87, telemetry module 88, and power source 98. Memory 82 may include computer-readable instructions that, when executed by processor 80, cause IMD 16 and processor 80 to perform various functions attributed to IMD 16 and processor 80 in this disclosure. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof.

Processor 80 controls signal generator 84 to deliver stimulation therapy to heart 12 according to operational parameters or programs, which may be stored in memory 82. For example, processor 80 may control stimulation generator 84 to deliver electrical pulses with the amplitudes, pulse widths, frequency, or electrode polarities specified by the selected one or more therapy programs.

Signal generator 84 is electrically coupled to electrodes 40, 42, 48, 50, 58, 62, and 66 of system 10 (FIGS. 1 and 2), e.g., via conductors of the respective lead 18 and 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver pacing pulses and CEWT to right atrium 26 via electrodes 48, 50, 58, and 66. Signal generator 84 may also deliver pacing pulses to right ventricle 28 via electrodes 40, 42, 58, and 62 and/or deliver cardioversion and/or defibrillation shocks to heart 12 via at least two electrodes 58, 62, and 66. In some examples, signal generator 84 delivers one or more of these types of stimulation in the form of electrical pulses. For example, signal generator 84 may deliver one or more of these types of stimulation as a single pulse or a train of electrical pulses. In other examples, signal generator 84 may deliver one or more of these types of stimulation in the form of other signals, such as sine waves, square waves, or other substantially continuous time signals.

Signal generator 84 may include a switch module, and processor 80 may use the switch module to select, e.g., via a data/address bus, which of the available electrodes are used to deliver stimulation signals, e.g., pacing, CEWT, cardioversion, and/or defibrillation signals. The switch module may include a switch array, switch matrix, multiplexer, or any other type of switching device suitable to selectively couple a signal to selected electrodes.

Electrical sensing module 86 monitors signals from at least one of electrodes 40, 42, 48, 50, 58, 62, or 66 in order to monitor electrical activity of heart 12. Electrical sensing module 86 may also include a switch module to select which of the available electrodes are used to sense the heart activity. In some examples, processor 80 may select the electrodes that function as sense electrodes, i.e., select the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in a respective chamber of heart 12, and may be configured to detect either R-waves or P-waves. In some examples, electrical sensing module 86 or processor 80 may include an analog-to-digital converter for digitizing the signal received from a sensing channel for electrogram (EGM) signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of electrodes 40, 42, 48, 50, 58, 62, or 66 appropriate for delivery of a bipolar or unipolar pacing pulse to one or more of the chambers of heart 12. Processor 80 may control signal generator to deliver a pacing pulse to a chamber upon expiration of an escape interval. Processor 80 may reset the escape interval counters upon the generation of pacing pulses by stimulation generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect heart rate, such as an atrial rate or ventricular rate. Processor 80 may also use the count in the interval counters to detect a high cardiac rate, such as a tachycardia event.

Processor 80 may also derive other physiological parameters from signals sensed via electrical sensing module 86. For example, processor 80 may establish one or more indicators of ejection fraction, stroke volume, cardiac efficiency, cardiac contractility, cardiac output, and/or heart failure status from electrical signals sensed via electrical sensing module 86. In particular, impedance signals may be used to determine flow or pressure, which may indicate one or more of ejection fraction, stroke volume, cardiac efficiency, cardiac contractility, cardiac output, and/or heart failure status.

IMD 16 may also include one or more sensors 87 separate from electrodes 40, 42, 48, 50, 58, 62, and 66. Via a signal generated by sensor 87, processor 80 may monitor one or more physiological parameters indicative of cardiac contraction, autonomic tone, heart failure status, and/or ejection fraction. Examples of sensors 87 that may generate a signal indicative of cardiac contraction include an intracardiac or intravascular pressure sensor, an accelerometer or other sensor capable of detecting heart or blood sounds, vibrations, or motion, an optical or ultrasonic sensor capable or detecting changes in flow associated with cardiac contractions, or an optical sensor capable of detecting oxygen saturation or tissue perfusion changes associated with cardiac contractions. Processor 80 may also detect one or more hemodynamic parameters via one or more sensors 87. For example, sensors 87 may monitor blood pressure in one or more of right ventricle 28, left ventricle 32, another chamber of heart 12, and an artery of patient 14. As one example, one or more of sensors 87 may monitor blood pressure within a pulmonary artery of patient 14. Processor 80 may detect blood pressure and/or other indicators of cardiac function based on signals from one or more sensors 87. For example, processor 80 may detect ventricular rate, stroke volume, cardiac efficiency, cardiac contractility, blood pressure, or cardiac output based on signals from one or more sensors 87.

In some examples, one or more of sensors 87 measure an activity level of patient 14. For example, sensors 87 may include one or more accelerometers. By monitoring the activity level of patient 14, e.g., whether patient 14 is resting or active, processor 80 may determine whether a detected heart rate, blood pressure, and/or other physiological parameters are at a level appropriate for the current activity level of patient 14.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

In some examples, processor 80 transmits information regarding atrial pacing and CEWT delivered by signal generator 84 via telemetry module 88. Processor 80 may also transmit, via telemetry module 88, a ventricular rate responsive to atrial pacing and CEWT, e.g., detected by electrical sensing module 86.

Figure 5:
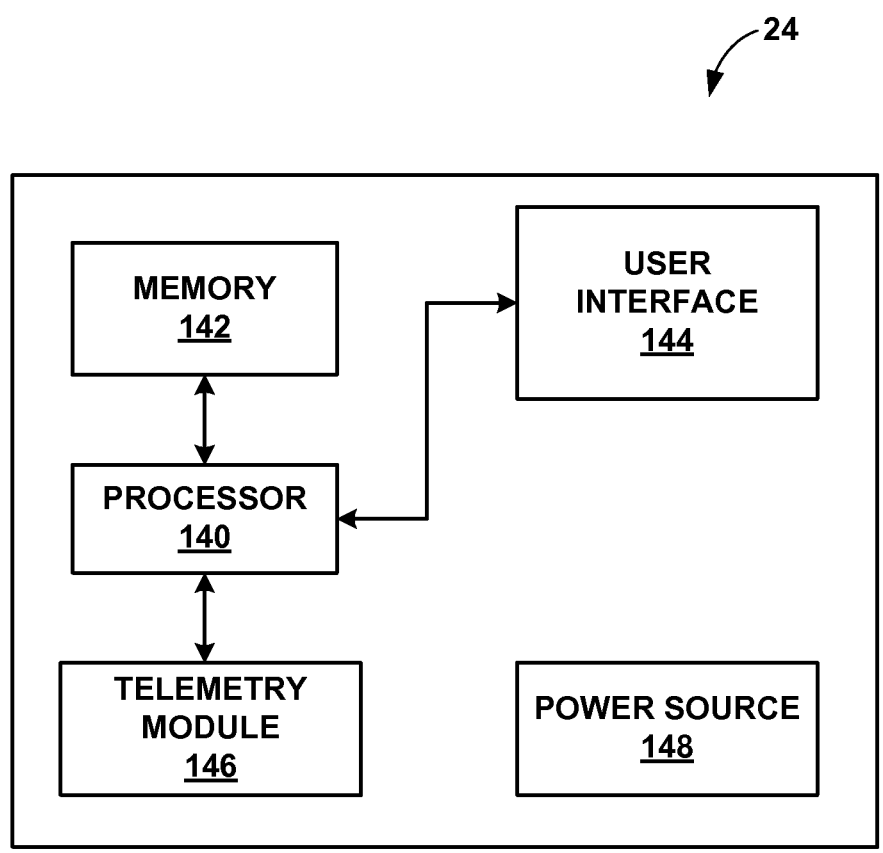
FIG. 5 is a block diagram of an example external programmer that facilitates user communication with the IMD.

FIG. 5 is a functional block diagram of an example configuration of programmer 24. As shown in FIG. 5, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, or modify therapy programs for IMD 16. The clinician may interact with programmer 24 via user interface 144, which may include a display to present a graphical user interface to a user, and a keypad or another mechanism for receiving input from a user.

Processor 140 can take the form one or more microprocessors, DSPs, ASICs, FPGAs, programmable logic circuitry, or the like, and the functions attributed to processor 140 in this disclosure may be embodied as hardware, firmware, software or any combination thereof. Memory 142 may store instructions that cause processor 140 to provide the functionality ascribed to programmer 24 in this disclosure, and information used by processor 140 to provide the functionality ascribed to programmer 24 in this disclosure. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 4).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 of programmer 24 and/or one or more processors of one or more networked computers may perform all or a portion of the techniques described in this disclosure with respect to processor 80 and IMD 16. For example, processor 140 or another processor may receive indications of heart rate, a signal from one or more sensors 87, information regarding other sensed parameters, or information regarding stimulus time windows associated with CEWT from IMD 16 via telemetry module 146. In some examples, processor 140 may initiate or modify atrial pacing and/or CEWT based on information sensed by sensing module 86 and/or sensors 87, as described in this disclosure with respect to IMD 16 and processor 80.

Figure 6:
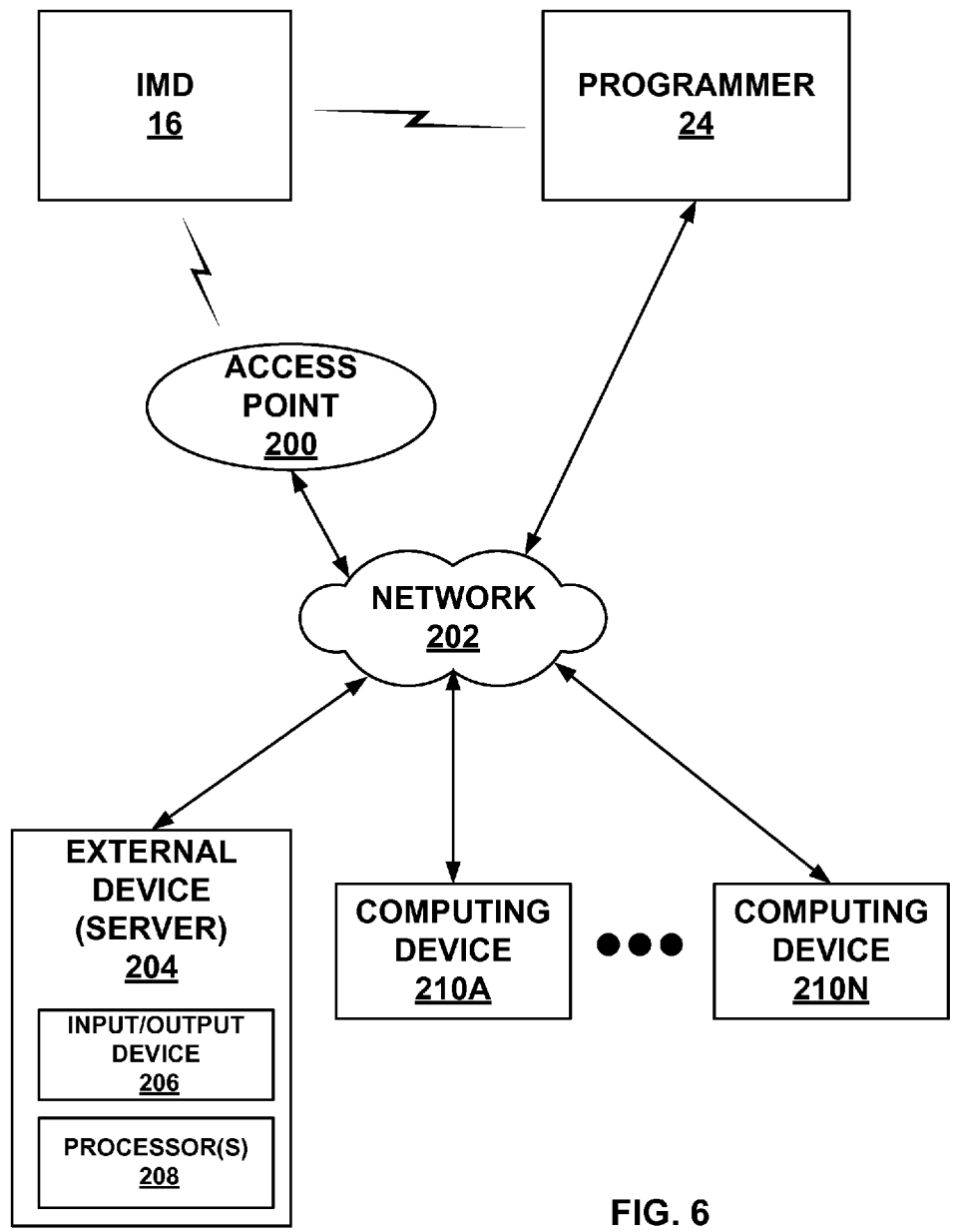
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described in this disclosure.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described in this disclosure. For example, access point 200 may include a home-monitoring unit that is co-located with patient 14 and that may monitor the activity of IMD 16. In some examples, server 204 or computing devices 210 may control or perform any of the various functions or operations described in this disclosure, e.g., initiate or modify atrial pacing and/or CEWT.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 206 may assemble data in web pages or other documents for viewing by trained professionals, such as clinicians, via viewing terminals associated with computing devices 210A-210N. The illustrated system of FIG. 6 may be implemented, in some aspects, with general network technology and functionality similar to that provided by the Medtronic CareLink® Network developed by Medtronic, Inc., of Minneapolis, Minn.

In some examples, processor 208 of server 204 may be configured to provide some or all of the functionality ascribed to processor 80 of IMD 16 in this disclosure. For example, processor 206 may receive indications of heart rate, a signal from one or more sensors 87, information regarding other sensed parameters, or information regarding stimulus time windows associated with CEWT from IMD 16 via access point 200 or programmer 24 and network 202. Processor 206 may also initiate or modify atrial pacing and/or CEWT based on information sensed by sensing module 86 and/or sensors 87, as described in this disclosure with respect to IMD 16 and processor 80. In some examples, server 204 relays indications of heart rate, a signal from one or more sensors 87, or other information regarding parameters sensed by sensing module 86 and/or sensors 87 provided by one or more of IMD 16 or programmer 24 to one or more of computing devices 210 via network 202. A processor of a computing device 210 may provide some or all of the functionality ascribed to processor 80 of IMD 16 in this disclosure. In some examples, a processor of computing device 210 may initiate or modify atrial pacing and/or CEWT.

Figure 7:
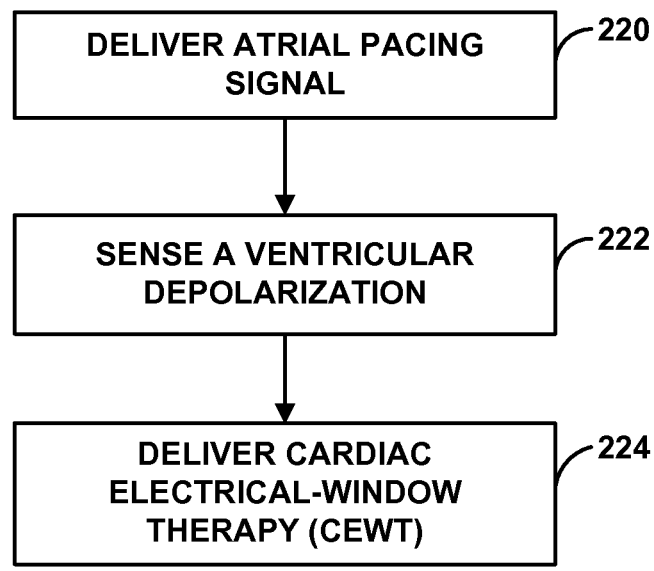
FIG. 7 is a flow diagram of an example method of delivering atrial pacing and cardiac electrical-window therapy (CEWT).
Figure 8:
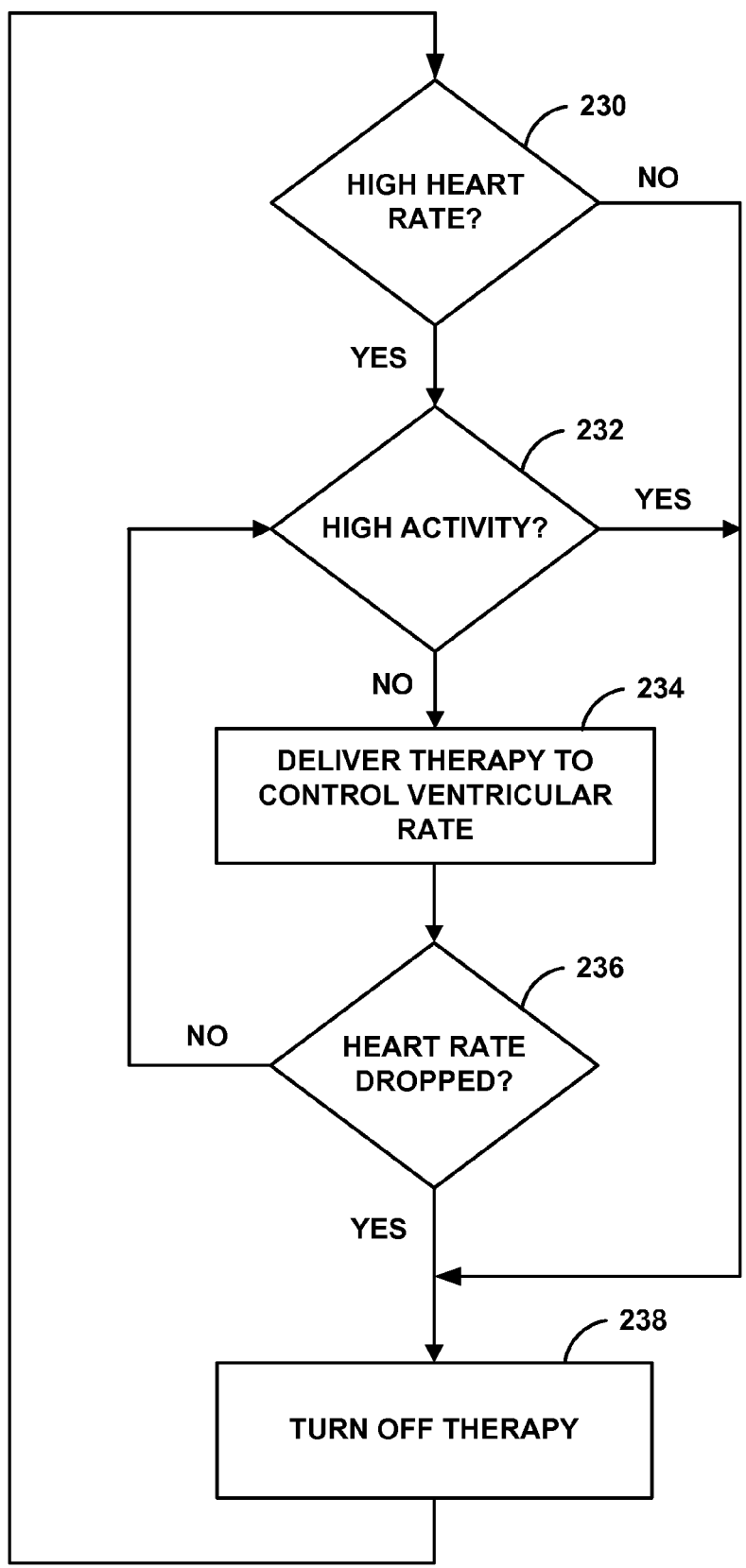
FIG. 8 is a flow diagram of an example method of activating atrial pacing and CEWT in response to a physiological parameter.
Figure 9:
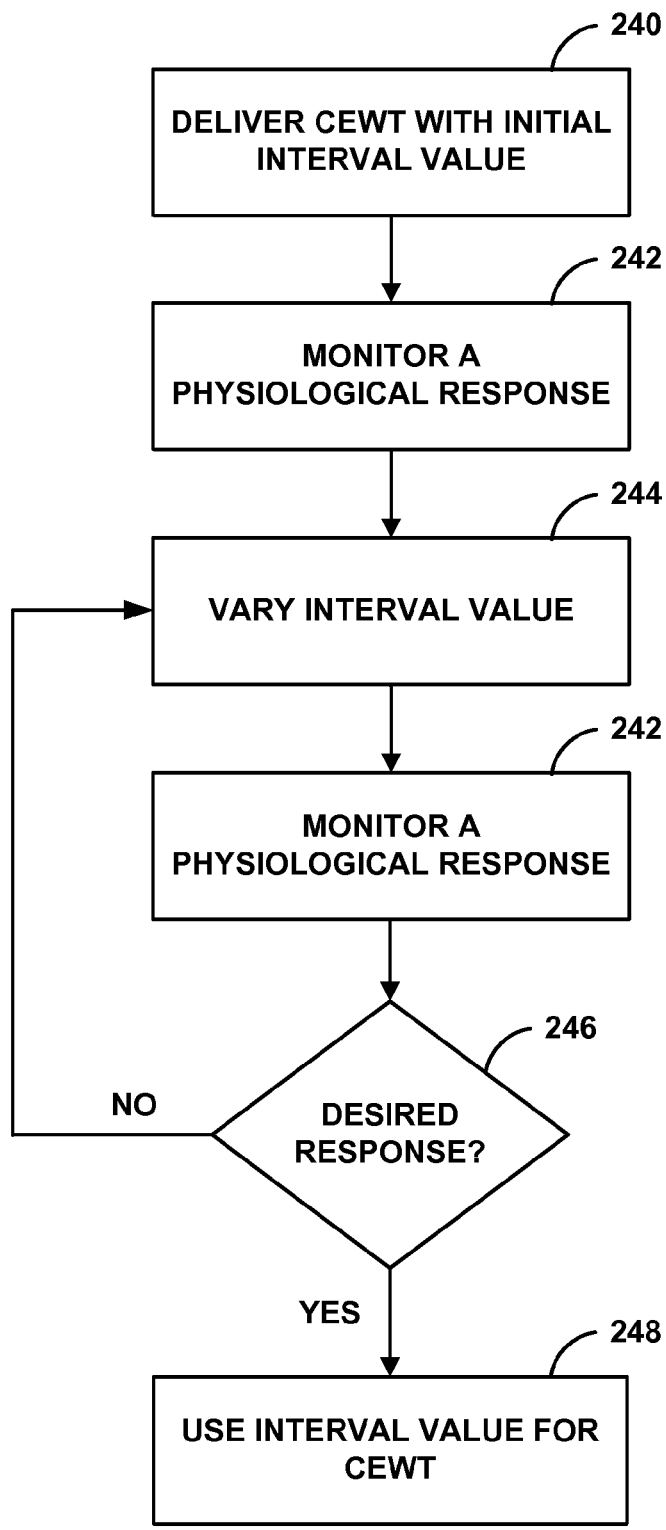
FIG. 9 is a flow diagram of an example method of adjusting the timing of CEWT.

FIGS. 7-9 describe example methods related to delivering atrial pacing and CEWT. The example methods of FIGS. 7-9 are described as being performed by processor 80 and sensing module 86 of IMD 16. In other examples, one or more other processors of one or more other devices may implement all or part of these methods.

FIG. 7 is a flow diagram of an example method of delivering atrial pacing and CEWT. Processor 80 controls signal generator 84 to deliver a pacing signal to right atrium 26, e.g., via any combination of electrodes 48, 50, 58, and 66 (220). The pacing signal may take the form of one or more pulses or other signals. In the example illustrated in FIG. 7, sensing module 86 senses a normally conducted ventricular depolarization subsequent to the atrial pacing signal (222). As described previously, a normally conducted ventricular depolarization may be a ventricular depolarization preceded by an atrial depolarization at an interval corresponding to a normal A-V conduction interval, i.e., not a premature ventricular depolarization. The ventricular depolarization may be intrinsic, paced or some combination of both, e.g., during delivery of ventricular resynchronization therapy.

Processor 80 controls signal generator 84 to deliver CEWT via electrodes 48, 50, and/or 66 during a stimulus time window in which the SAN, atria 26 and 36, and/or AVN 30 may be excited while ventricles 28 and 32 remain refractory to stimulation (224). For example, processor 80 may control signal generator 84 to deliver a CEWT signal in the form of one or more pulses or other signals. In the example of FIG. 7, the stimulus time window is based on the timing of the normally conducted ventricular depolarization detected by sensing module 86 subsequent to the atrial pacing signal delivered by signal generator 84. For example, processor 80 may control signal generator 84 to deliver CEWT within a time period occurring between about 80 ms to about 200 ms following the normally conducted ventricular depolarization detected by sensing module 86.

In other examples, processor 80 may control signal generator 84 to deliver CEWT within a defined time period following the atrial pacing signal. In such examples, it may not be necessary for sensing module 86 to detect the normally conducted ventricular depolarization. However, in some examples, processor 80 may require that sensing module 86 detects the normally conducted ventricular depolarization to confirm its occurrence prior to controlling signal generator 84 to deliver CEWT. In other examples, processor 80 may utilize the timing of both the paced atrial depolarization and the ventricular depolarization, e.g., paced or sensed, to determine the CEWT delivery time or the permitted range of delivery times, i.e., the stimulus time window.

Processor 80 may control signal generator 84 to deliver CEWT using stimulation parameters of typical cardiac pacing pulses or pulse bursts having burst envelopes corresponding to the duration and/or morphology of normal cardiac pacing pulses. Longer pulse durations, e.g. 10 milliseconds (ms) or more, or trains of pulses may also be employed. In some examples, signal generator 84 delivers CEWT using an amplitude in the range of approximately 1 volt to approximately 2 volts and a pulse width of approximately 0.5 ms to approximately 1 ms.

FIG. 8 is a flow diagram of an example method of activating atrial pacing and CEWT in response to a physiological parameter. Processor 80 monitors a heart rate of patient 14, e.g., based on cardiac depolarizations detected by sensing module 86 (230). If the heart rate is elevated, e.g., above a threshold value, processor 80 may cross check the detected heart rate with a physiological sensor, such as an activity sensor, to determine whether the detected heart rate is appropriate (232). If the heart rate is determined to be excessive, processor 80 initiates atrial pacing and CEWT, e.g., according to the method described with respect to FIG. 7 (234). The combination of atrial pacing and CEWT may allow IMD 16 to control the ventricular rate of patient 14.

Processor 80 may determine, e.g., periodically, whether the heart rate of patient 14 has dropped (236). In some examples, processor 80 may control signal generator 84 to pause atrial pacing and CEWT to allow sensing module 86 to detect the heart rate of patient 14 when it is not being controlled by these therapies. If the heart rate of patient 14 has dropped, which may be crossed checked with a physiological signal to confirm that the heart rate is appropriate, processor 80 turns the atrial pacing and CEWT therapies off (238). If the heart rate has not dropped, processor 80 may once again cross check the detected heart rate with a physiological sensor, such as an activity sensor, to determine whether the detected heart rate is appropriate (232) and continue to control signal generator 84 to deliver atrial pacing and CEWT (234) or turn off the atrial pacing and CEWT therapies (238) based on the determination.

Although FIG. 8 is described with respect to heart rate, processor 80 may control the delivery of atrial pacing and CEWT based on other physiological parameters. As one example, processor 80 may control signal generator 84 to deliver atrial pacing and CEWT responsive to a sensed inappropriately high blood pressure, e.g., exceeding a threshold value. In other examples, processor 80 may control signal generator 84 to deliver atrial pacing and CEWT responsive to other indicators of cardiac functions. Processor 80 may activate signal generator 84 to deliver atrial pacing and CEWT when such parameters exceed or fall below a threshold value and turn off therapy when such parameters exceed or fall below a threshold value, as appropriate. As an example, processor 80 may activate signal generator 84 to deliver atrial pacing and CEWT based on one or more of ventricular rate, stroke volume, cardiac efficiency, cardiac contractility, blood pressure, or cardiac output.

FIG. 9 is a flow diagram of an example method of adjusting the timing of CEWT. Processor 80 may control signal generator 84 to deliver CEWT with an initial interval value (240). The initial interval may be timed from the atrial pacing signal and/or the ventricular depolarization that follows the paced atrial depolarization, as discussed above. Processor 80 may select the initial value of the interval to, for example, fall near the beginning, middle, or end of the stimulus time window.

Processor 80 monitors a physiological response to CEWT via sensing module 86, e.g., by monitoring one or more parameters that varies in response to CEWT (242). For example, processor 80 may monitor ventricular rate, blood pressure, and/or another parameter indicative of cardiac function, such as stroke volume, cardiac efficiency, cardiac contractility, or cardiac output. Processor 80 increases or decreases the interval and controls signal generator 84 to deliver CEWT with the new interval value (244). Processor 80 monitors a physiological response to CEWT with the new interval via sensing module 86 (242).

Processor 80 may continue to control signal generator 84 to deliver CEWT with various interval values (244) and monitor the physiological response (242) until a desired response is achieved (246). Processor 80 may select the interval value that produced the desired response for CEWT (248). In some examples, processor 80 stores the interval value in memory 82 for future use. The desired response may be a minimum obtainable level for heart rate or blood pressure, or a heart rate or blood pressure below a threshold value, or as close as possible to either one. The threshold value for blood pressure or heart rate may be determined based upon the output of a physiological sensor, such as an activity sensor. Other desired responses are possible and may be based on other indicators of cardiac function, such as stroke volume, cardiac efficiency, cardiac contractility, or cardiac output. Processor 80 may accomplish variation of the interval by means of gradual increase or decrease of the interval value or by means of a binary search type operation.

Values of other stimulation parameters, e.g., amplitude, pulse width, may be stored in memory 82 as part of a CEWT program. However, in some examples, a method analogous to the method described with respect to FIG. 9 may be employed to determine values of other stimulation parameters. The method of determining an interval value described with respect to FIG. 9 may be performed, for example, when processor 80 initiates CEWT for the first time, e.g., in conjunction with atrial pacing.

Atrial pacing and CEWT may be used to treat a variety of conditions. Reducing heart rate and/or blood pressure may be beneficial to patients who suffer from supraventricular tachycardia (SVT), hypertension, heart failure, or myocardial ischemia. Currently, these conditions are largely treated by drugs, not by medical devices, with the exception of cardiac defibrillation and cardiac resynchronization therapy. Therefore, medical device therapy reducing heart rate and/or blood pressure may open up significant opportunities to treat those aforementioned diseases. Also, the device-based therapy may provide an option to patients who do not respond well to drug therapy or have severe side effects. A device-based therapy, as described in this disclosure, may reduce dependence on drug therapy and decrease drug-induced side effects.

A scientific study was performed on two porcine models to investigate the effects of atrial pacing and CEWT. Three device were implanted in each porcine model (n=2)—one Concerto® cardiac resynchronization therapy-defibrillator (CRT-D) (commercially available from Medtronic, Inc. of Minneapolis, Minn.) for CEWT delivery, one EnRhythm® (commercially available from Medtronic, Inc. of Minneapolis, Minn.) for myocardial electrogram (EGM) data collection and high-rate atrial pacing, and one PhysioTel® PA-D70 device (commercially available from Data Sciences International of Saint Paul, Minn.) for blood pressure monitoring.

The Concerto® device was connected with one lead placed in the AVN area for CEWT stimulation and another lead placed in the right ventricle (RV) apex for sensing ventricular depolarizations used to trigger CEWT. The EnRhythm® device was connected with one lead placed in the RV septum for periodic EGM data collection and another lead placed in the right atrial appendage (RAA) for periodic EGM data collection and atrial pacing. The PhysioTel® PA-D70 device was connected with a catheter inserted into one carotid artery for blood pressure monitoring. Each animal had a five day recovery after the surgical operation and then CEWT was turned on or off as needed for the experiment. The effects of CEWT on heart rate and blood pressure were monitored for two weeks. The effects of CEWT on cardiac output, coronary blood flow, and myocardial oxygen consumption were assessed during terminal experiments.

The control heart rate measured in full consciousness was 105±1.2 beats per minute (bpm) (mean±standard error (SE) for 12 days). During CEWT treatment, the heart rate was significantly decreased to 77±0.9 bpm (mean±SE for 9 days) ($p<0.00001$). Blood pressure was also decreased. The systolic pressure was decreased from 166±1 mm Hg (control) to 158±2 mm Hg (CEWT), and the diastolic blood pressure was decreased from 141±3 mm Hg (control) to 115±1 mm Hg (CEWT, $p<0.0001$).

The stimulus time windows measured under anesthesia and in full consciousness were very similar, 220 ms under anesthesia with a heart rate of 108 bpm and 200 ms in full consciousness with a heart rate of 110 bpm. The stimulus time window was 210 ms measured in full consciousness with a pacing heart rate of 150 bpm by pacing the RAA. Injection of the β-adrenergic agonist isoproterenol and the muscarinic antagonist atropine effectively induced tachycardia by increasing the heart rates to 137 bpm and 158 bpm, respectively. The corresponding stimulus time windows for CEWT were 170 ms for isoproterenol and 200 ms for atropine.

During the terminal experiments, CEWT reduced the heart rate, blood pressure, cardiac output, systemic vascular resistance and left anterior descending artery (LAD) blood flow with or without right atrial high-rate pacing or drug-induced hypertension. However, CEWT increased the right atrial pressure, stroke volume, and LAD blood flow/per beat. CEWT significantly decreased the myocardial $O_2$ consumption, especially during drug-induced hypertension.

CEWT significantly reduced the ventricular rate in conscious animals. CEWT also significantly reduced the blood pressure in conscious animals, especially during experimental hypertension. Also, the sizes of CEWT stimulus time windows measured in anesthetized and conscious animals were similar, and the sizes of the stimulus time windows did not markedly vary in conscious animals during experimental tachycardias with rates less than 160 bpm. Additionally, CEWT significantly reduced myocardial $O_2$ consumption, especially during experimental hypertension.

Figure 10:
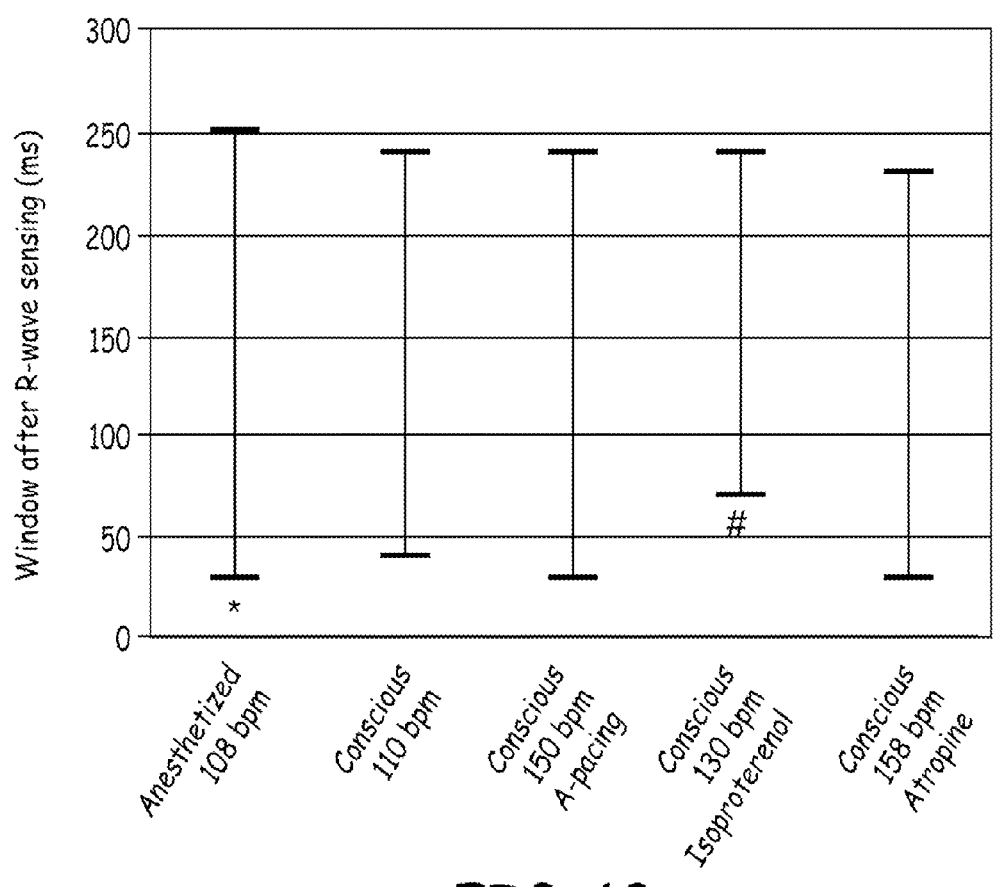
FIGS. 10-21 illustrate data collected during a scientific study performed to investigate the effects of atrial pacing and CEWT.

FIG. 10 illustrates the sizes of CEWT stimulus time windows measured under anesthetized or conscious conditions with or without other challenges. Within these time ranges CEWT effectively reduced the ventricular rate. The ventricular axis illustrates the time delay for CEWT delivered to the atrium after sensing the R-wave. The data in the figure was obtained from one animal. The stimulation pulse for CEWT had a width of 1 ms and a magnitude of 2 volts (V). * indicates the shortest latency (30 ms) could go with the current refractory period stimulation (RPS) program. # indicates that shorter durations were not tested as the animal was active at that time.

The sizes of CEWT stimulus time windows were very similar when measured under anesthetized or awaken conditions. High-rate atrial pacing of the RAA and drug-induced tachycardias (<160 bpm) also did not markedly reduce the size of the stimulus time window. These results indicate that within a certain range of heart rates, the stimulus time window for CEWT remains relatively constant. The change in the stimulus time window for CEWT was minor. Therefore, the CEWT pulses may be reliably delivered within the stimulus time window, which may help assure that the desired effect is produced without induction of arrhythmias.

Figure 11:
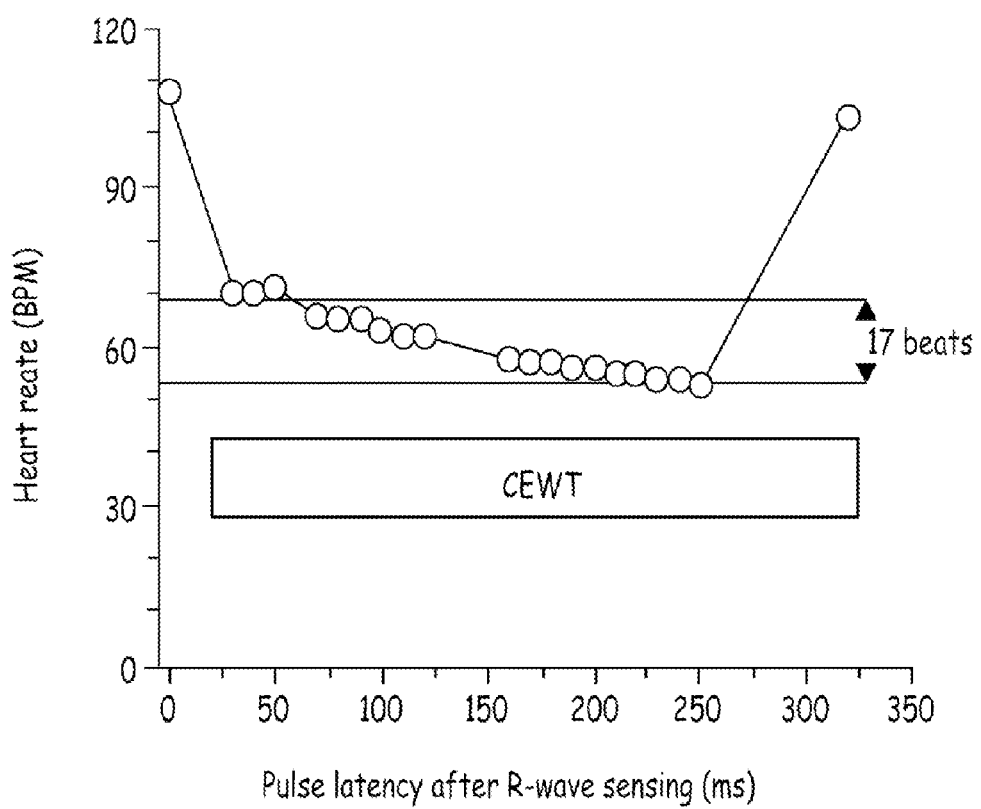

FIG. 11 illustrates the effects of CEWT on the ventricular rates with various pulse latencies. The pulse width of the CEWT stimulation was 1 ms and the amplitude was 2V. The effects of CEWT on the ventricular rates varied with the latencies of the stimulation pulses. The variance was in the range of 17 bpm. As illustrated in FIG. 11, the ventricular rate was decreased from 108 bpm to 70 bpm with the pulse latency <50 ms. Following the prolongation of pulse latency, the ventricular rates gradually decreased more. The ventricular rate decreased to 53 bpm when the pulse latency was set at 250 ms after sensing the R-wave. These results suggest that CEWT can regulate the level of ventricular rate reduction in a certain range by using different pulse latencies.

Figure 12:
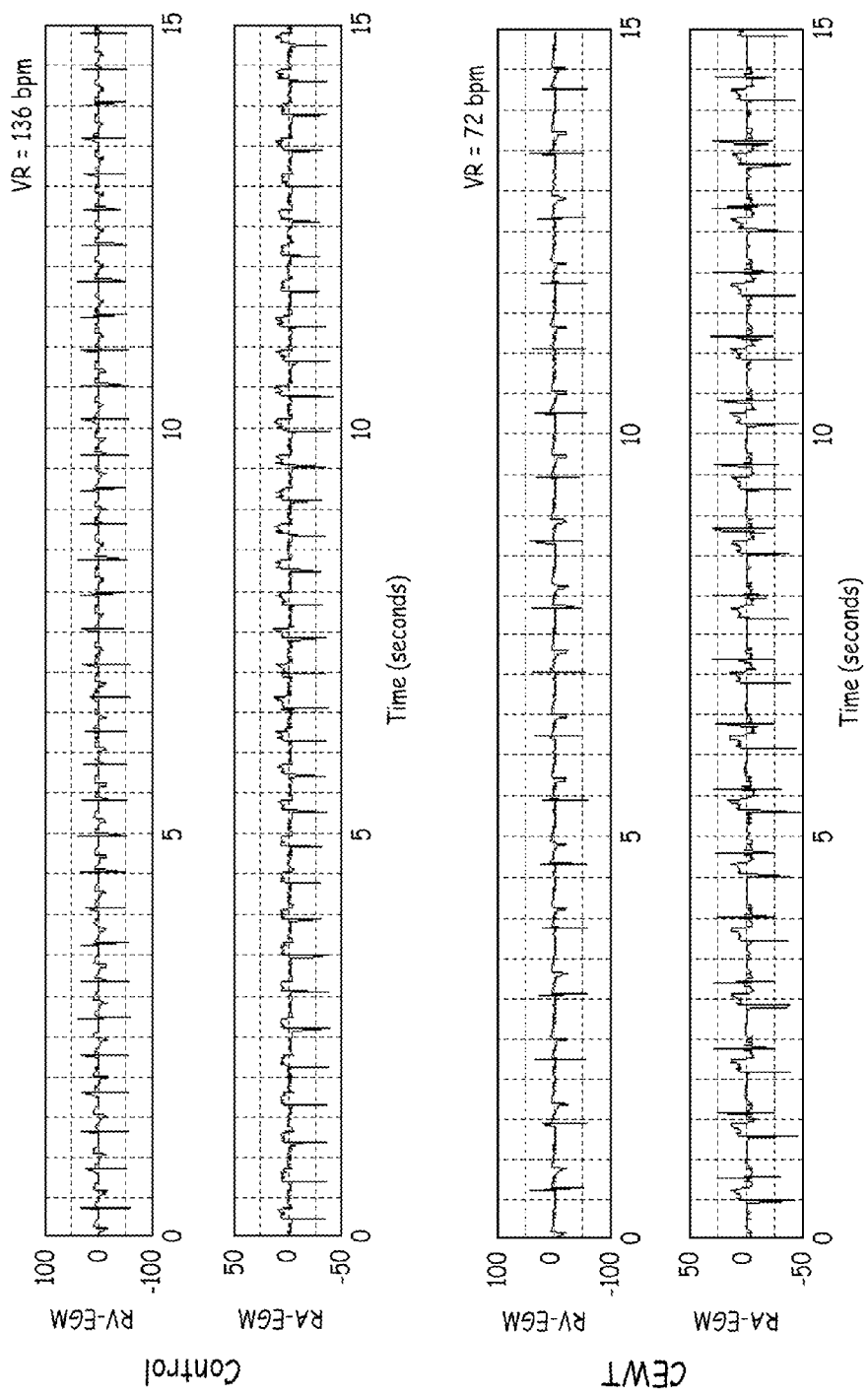

FIG. 12 illustrates the effects of CEWT on ventricular rate in conscious porcine. The data were downloaded from the implanted EnRhythm® device during a monitoring period when the porcine were conscious. CEWT stimulation pulses were set at 1 ms and 2V with a delay of 90 ms after sensing R-wave. The top two rows illustrated in FIG. 12 are the control EGMs (control) recorded from the RAA lead and the RV lead for 15 seconds (s), and the bottom two rows are the EGMs recorded from the same leads when CEWT was turned on (CEWT). As illustrated in FIG. 12, the ventricular rate as determined from the right ventricular EGM decreased when CEWT was on. More specifically, CEWT decreased the ventricular rate from 136 bpm for the control to 72 bpm for CEWT in a freely moving and fully conscious porcine.

Figure 13:
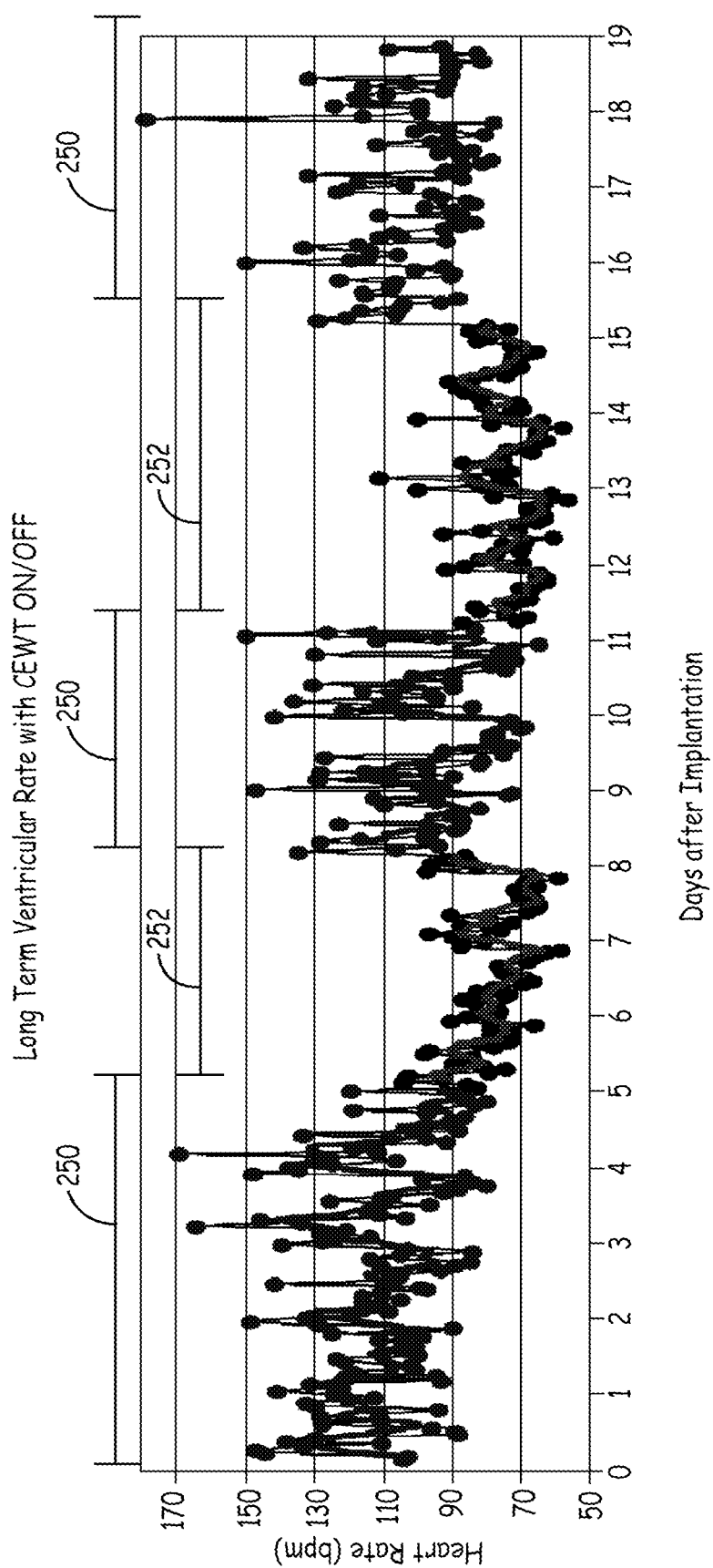

FIG. 13 illustrates the time course of the heart rates after device implantation with and without CEWT on. The regions 250 illustrate the heart rates collected when CEWT was off. The regions 252 represent the ventricular rates collected when CEWT was on. Each data point represents an averaged rate of each heart rate calculated from recorded EGM data. The CEWT pulse parameters were 1 ms and 2V.

In conscious animals, the heart rates were variable over time, even with CEWT on. FIG. 13 illustrates the time course of the heart rates during the whole observation period (19 days). However, the rates when CEWT was on, as shown in regions 252, were significantly lower than those when CEWT stimulation was off, as shown in regions 250. The variabilities of the heart rates ranged from approximately 70 to approximately 170 bpm during controls and from approximately 60 to approximately 110 bpm when CEWT was on. These rate changes may be due to physical activities, feeding, or other interferences. The averaged ventricular rate was significantly decreased during CEWT, 105.2±1.2 bpm for control and 77.5±0.9 bpm for CEWT, respectively, as shown in FIG. 14.

Figure 14:
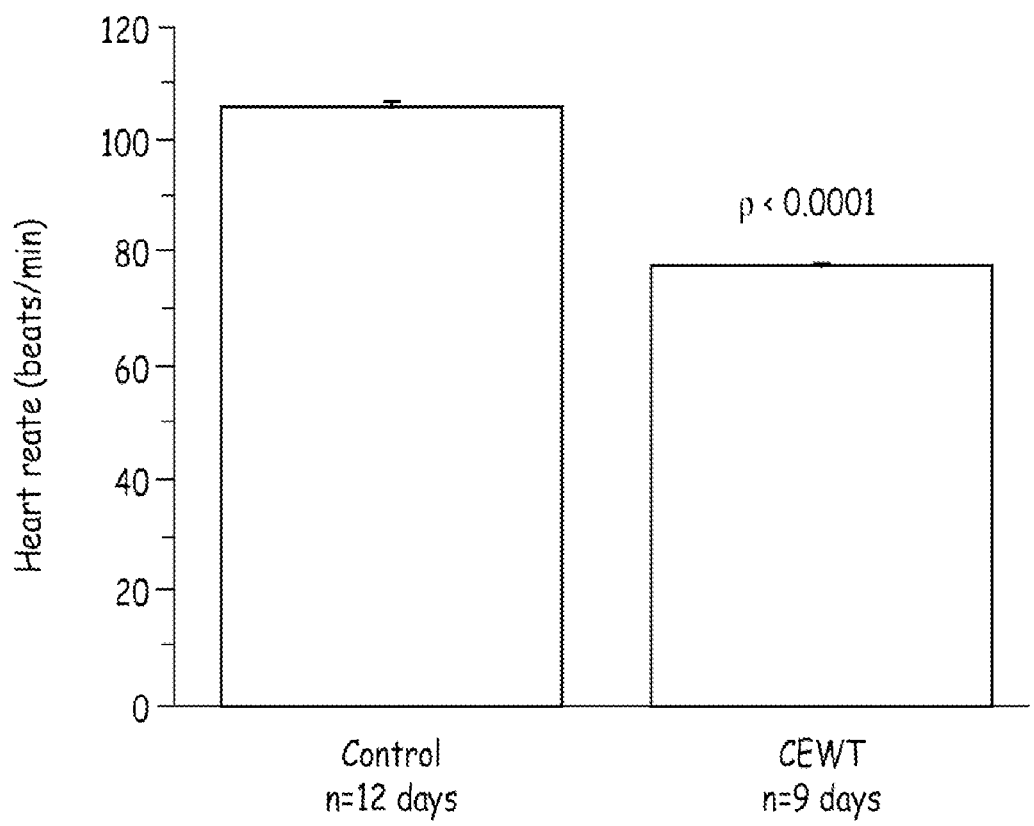

FIG. 14 illustrates the averaged heart rates during a 12 day control period (105.2±1.2 bpm) and a 9 day period with CEWT on (77.5±0.9 bpm).

Figure 15:
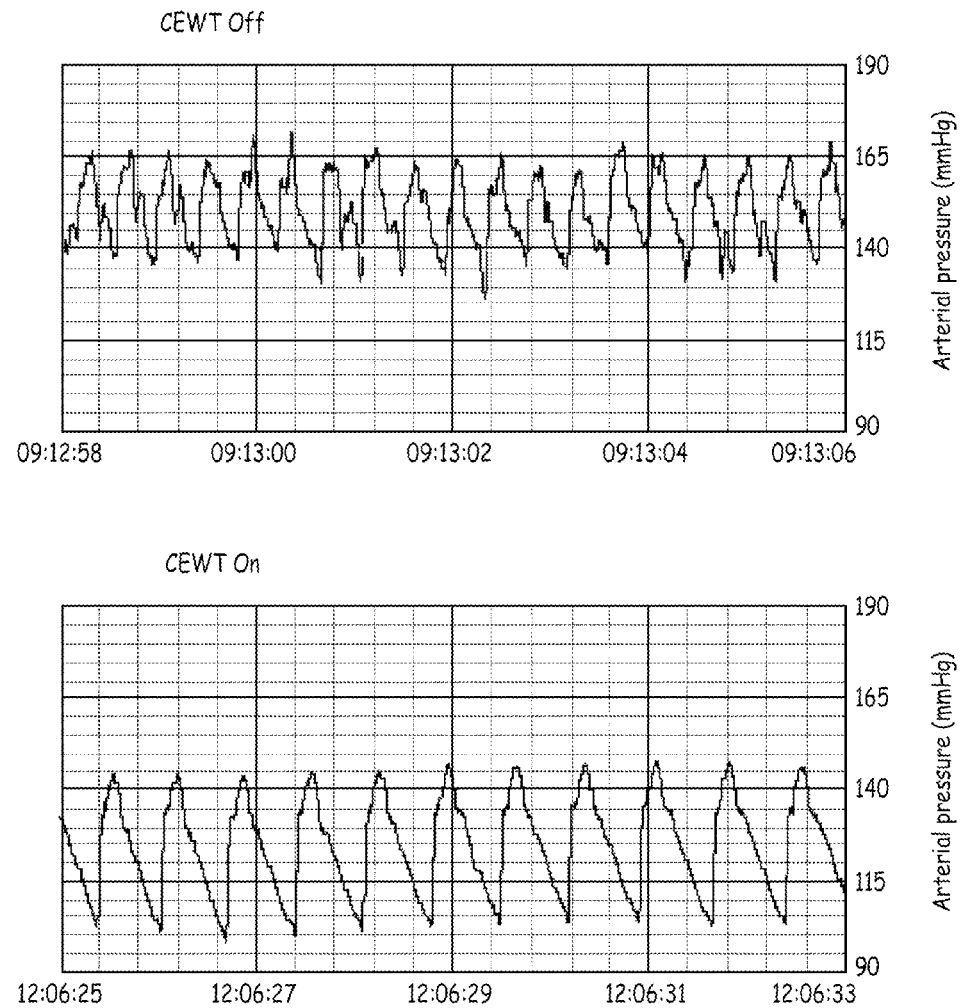

FIG. 15 illustrates the effects of CEWT on porcine blood pressure. The blood pressure traces were collected during awake monitors on different days via the implanted Physio-Tel® PA-D70 data collection system. The upper panel illustrates the representative arterial pressure traces recorded before CEWT was turned on as a control, and the lower panel illustrates the representative arterial pressure traces recorded when CEWT was on.

As illustrated in FIG. 15, both the systolic pressure and diastolic pressure were markedly decreased when CEWT was turned on. The systolic pressure was decreased from approximately 165 mm Hg for the control to approximately 145 mm Hg for the CEWT treatment. The diastolic pressure was decreased even more, from approximately 135 mm Hg for the control to approximately 102 mm Hg for CEWT. The pulse rate was decreased from 142 bpm for the control to 85 bpm for CEWT.

Figure 16:
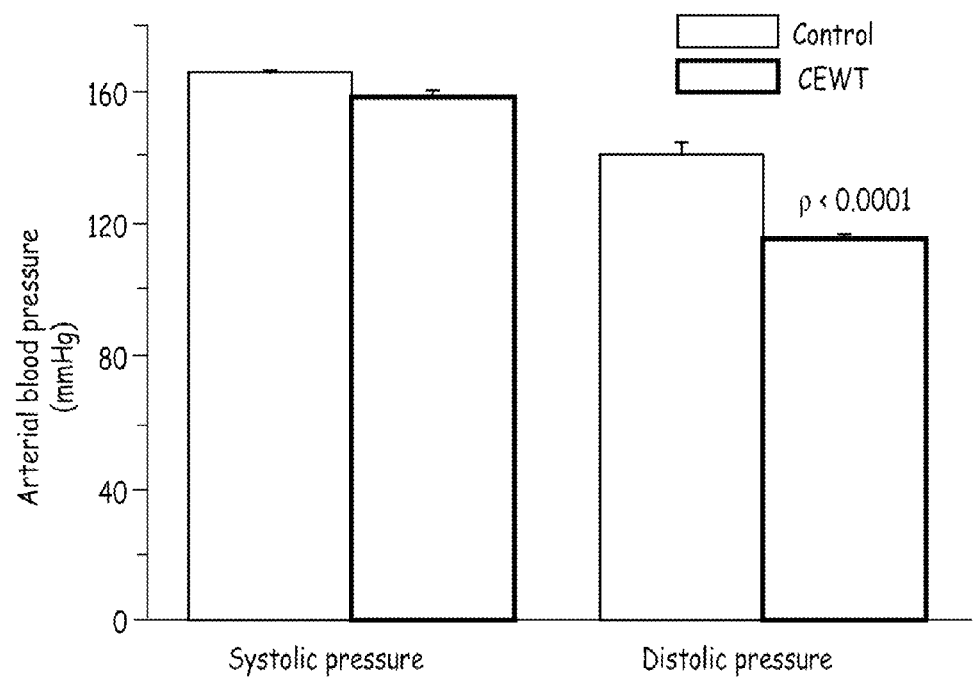

FIG. 16 illustrates the decreases in systolic and diastolic blood pressures by CEWT treatment. The averaged data for the control was obtained from 2 days of observations, and the pressures for CEWT treatment were obtained from 6 days of monitoring. The average decreases in blood pressure obtained from all of the awake monitors with CEWT treatment were 7.5 mmHg for the systolic pressure (p>0.05) and 26 mmHg for the diastolic pressure (p<0.0001), respectively.

Figure 17:
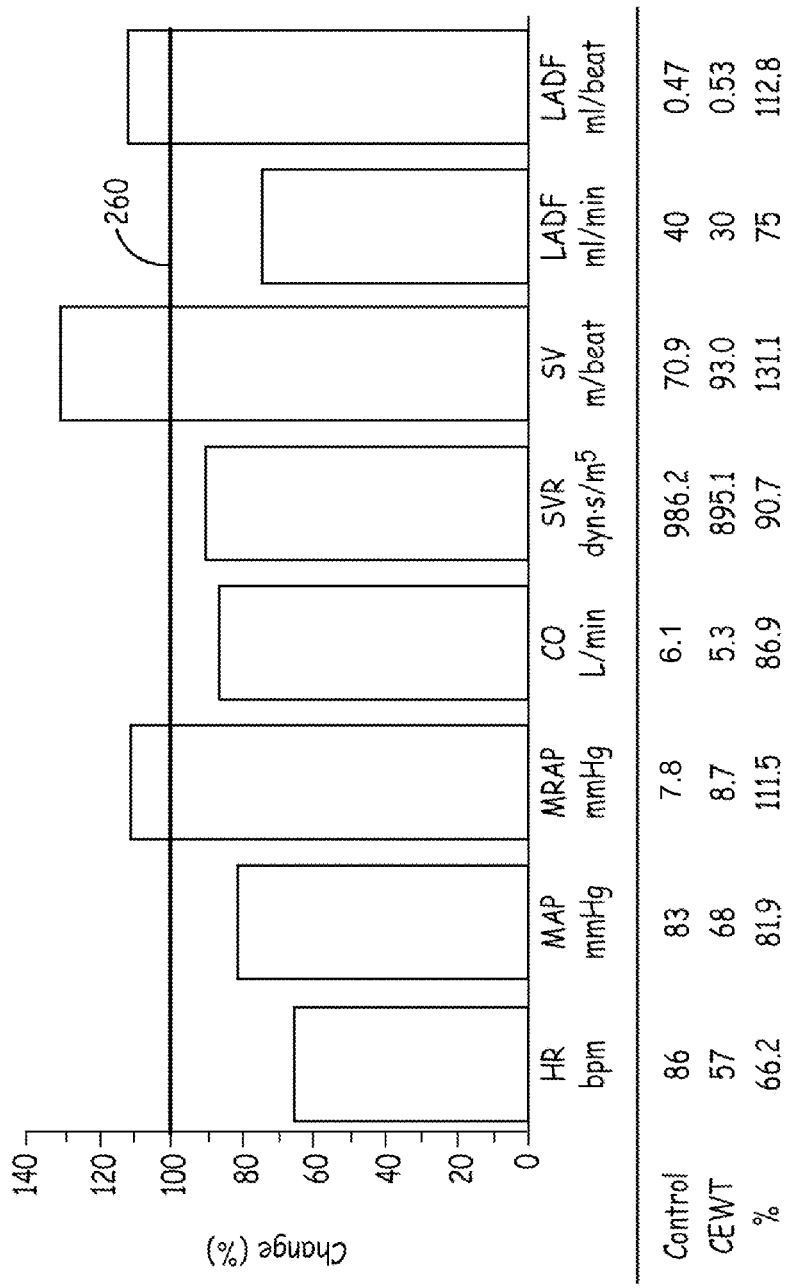

FIG. 17 illustrates the effects of CEWT on hemodynamics and cardiac function in anesthetized porcine. Heart rate (HR), mean arterial blood pressure (MABP), and mean right atrial pressure (MRAP) were measured with a catheter placed into the right atrium. Cardiac output (CO) was measured with a flow probe placed at the root of the aorta. Systemic vascular resistance (SVR) was calculated using the equation: SVR=[(MAP−CVP)×80]/(CO). Stroke volume (SV) and blood flow of the coronary left anterior descending artery (LADF) were measured with a flow probe in units of milliliters (ml) per beat and ml per minute (min), respectively. Percent changes were calculated by dividing the values measured during CEWT by the corresponding values of the control. Horizontal line 260 represents a level of 100%.

Figure 18:
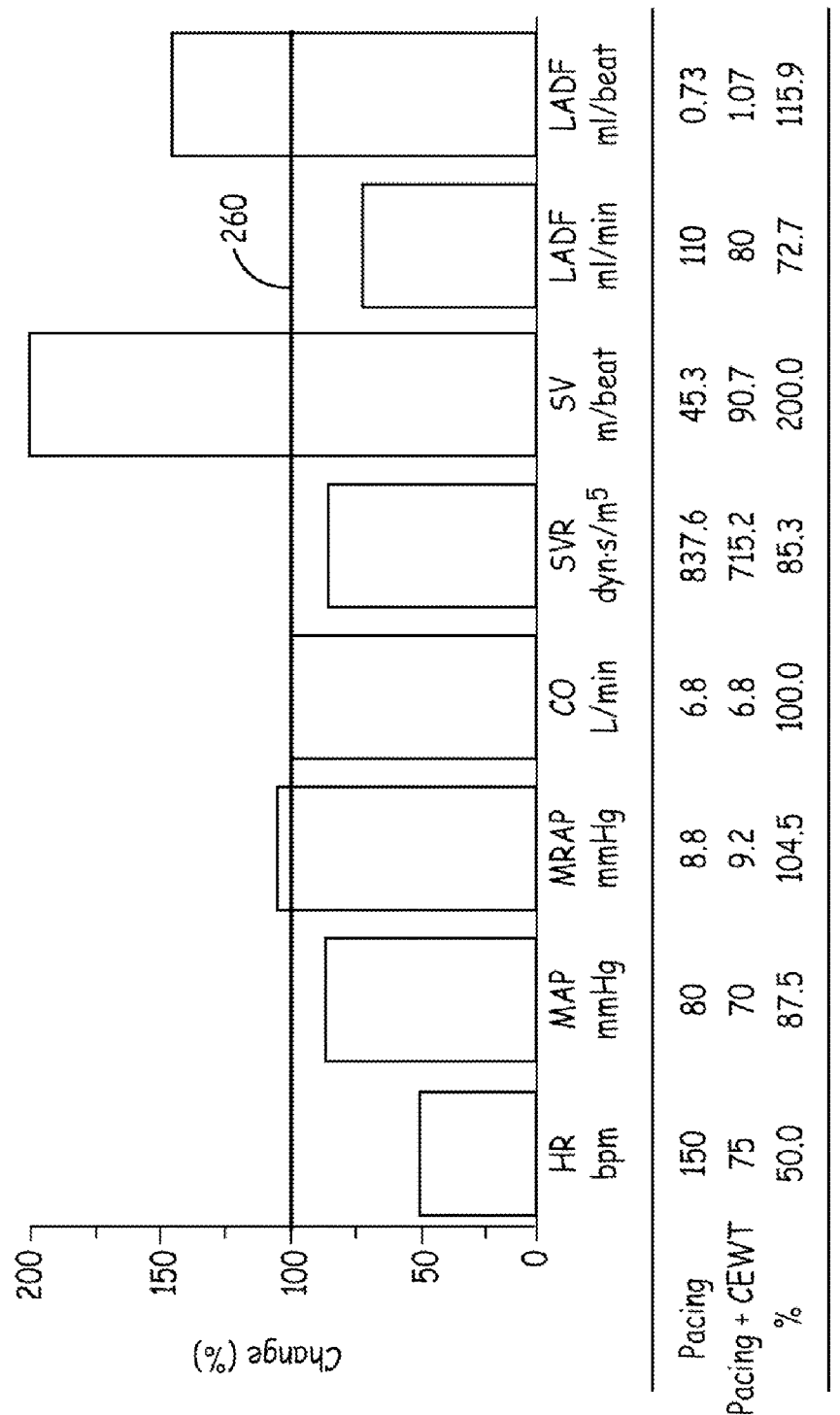

FIG. 18 illustrates the effects of CEWT on hemodynamics and cardiac function during high-rate right atrial pacing in anesthetized porcine. Percent changes were calculated by dividing the values during (pacing+CEWT) by the corresponding values during pacing alone. Horizontal line 260 represents a level of 100%.

Figure 19:
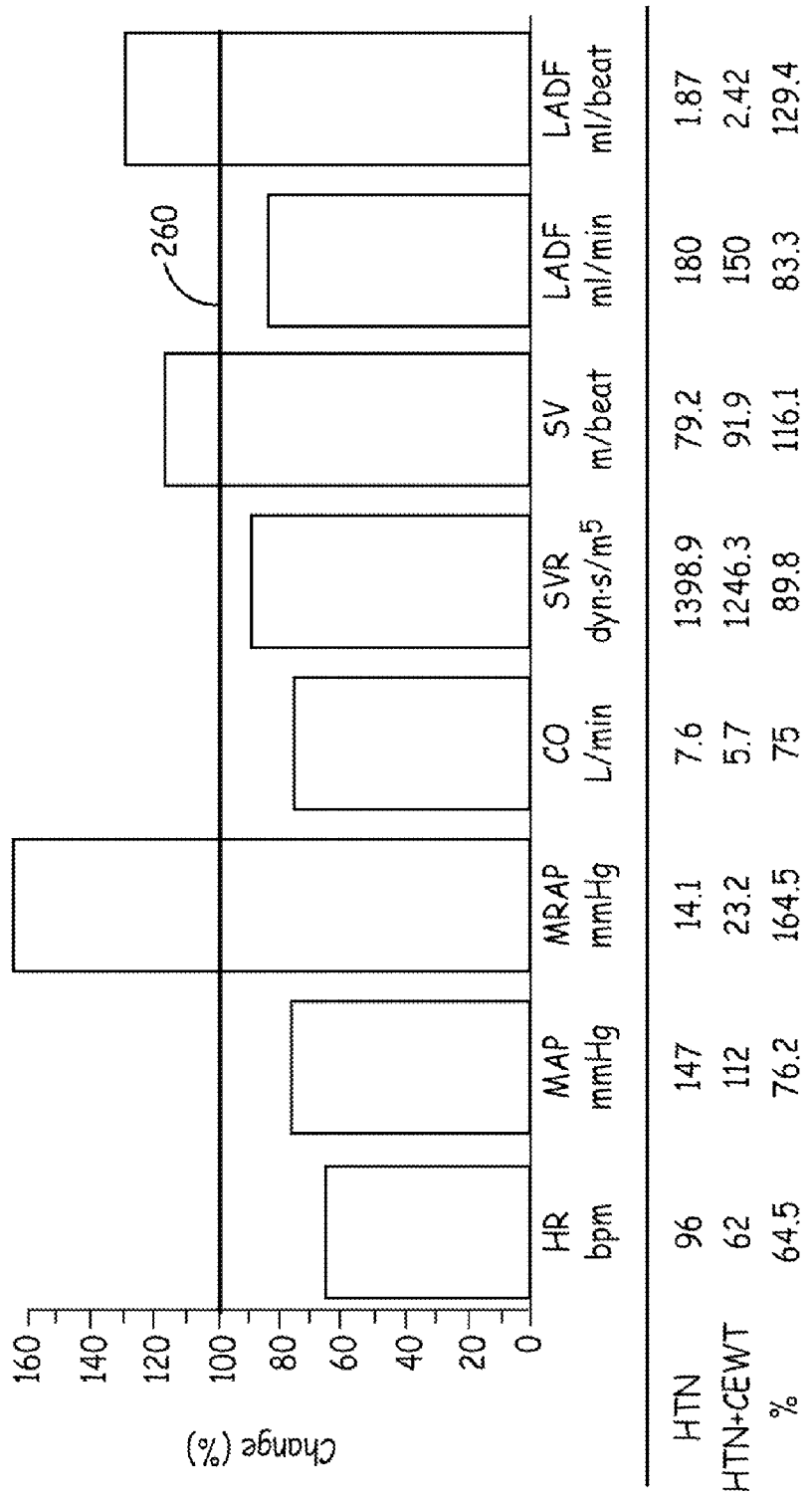

FIG. 19 illustrates the effects of CEWT on hemodynamics and cardiac function during drug-induced hypertension (HTN) in anesthetized porcine. Percent changes were calculated by dividing the values during (HTN+CEWT) by the corresponding values during HTN alone. Horizontal line 260 represents a level of 100%.

Figure 20:
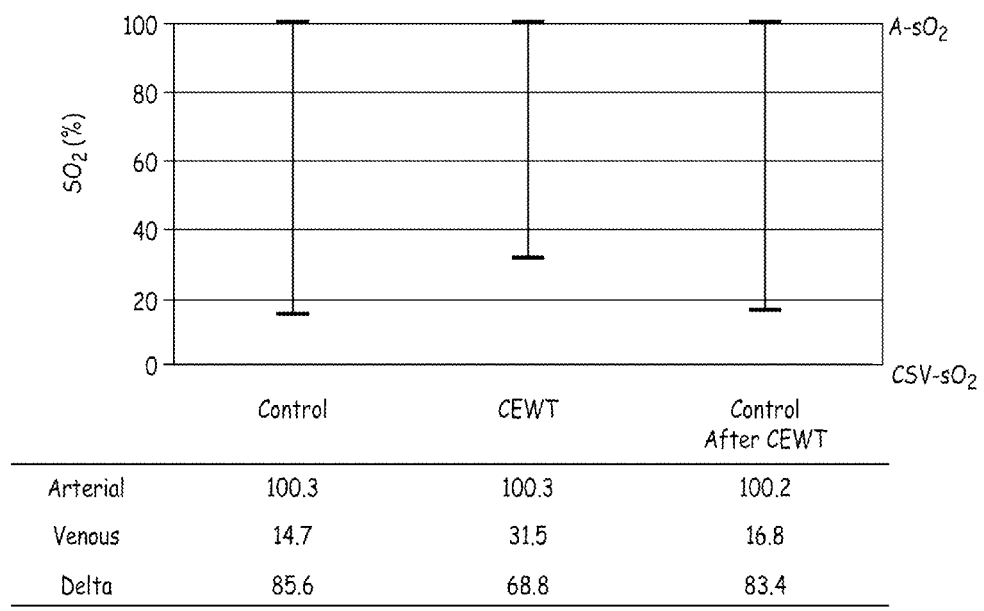

FIG. 20 illustrates the effects of CEWT on blood oxygen extraction in the anesthetized porcine. Blood samples (2 ml/per sample) were drawn from the carotid artery and the coronary sinus five minutes before CEWT was turned on (Control), five minutes after CEWT was turned on (CEWT), and five minutes after CEWT was turned off (Control After CEWT). Oxygen saturation levels in the blood ($sO_2$) were measured. In particular, oxygen saturation in arterial blood (A-$sO_2$) and oxygen saturation in coronary sinus venous blood (CSV-$sO_2$) were measured. The deltas in the low panel of FIG. 20 represent the differences of the oxygen contents between the arterial and coronary venous blood.

Figure 21:
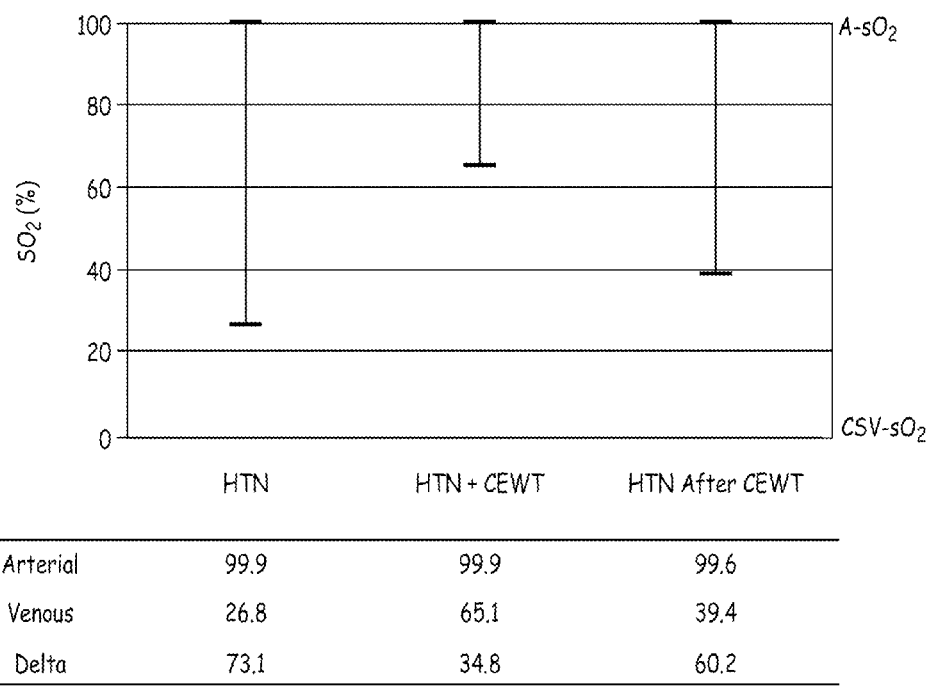

FIG. 21 illustrates the effects of CEWT on arterial and coronary venous oxygen saturation during drug-induced hypertension (HTN) in the anesthetized porcine. Blood samples (2 ml/per sample) were drawn from the carotid artery and coronary sinus five minutes before HTN, five minutes after CEWT was turned on (HTN+CEWT) and five minutes after CEWT was turned off (HTN after CEWT). Oxygen saturation levels in the blood ($sO_2$) were measured. In particular, oxygen saturation in arterial blood (A-$sO_2$) and oxygen saturation in coronary sinus venous blood (CSV-$sO_2$) were measured. The deltas in the low panel of FIG. 21 represent the differences of the oxygen contents between the arterial and coronary venous blood Various examples of the disclosure have been described. These and other examples are within the scope of the following claims.

The invention claimed is:

1. A method comprising: delivering a pacing signal configured to cause an atrial depolarization to a heart of a patient having intact A-V conduction, wherein the atrial depolarization results in an associated refractory period during a cardiac cycle; and delivering a signal to a supraventricular portion of the heart of the patient subsequent to the atrial refractory period and during a ventricular refractory period of the cardiac cycle.

2. The method of claim 1, wherein delivering the signal to the supraventricular portion of the heart comprises delivering the signal to at least one of an atrium, a sinoatrial node, or an atrioventricular node of the heart of the patient.

3. A method comprising: delivering a pacing signal configured to cause an atrial depolarization to a heart of a patient, wherein the atrial depolarization results in an associated refractory period during a cardiac cycle; and delivering a signal to a supraventricular portion of the heart of the patient subsequent to the atrial refractory period and during a ventricular refractory period of the cardiac cycle; and
   further comprising detecting a ventricular depolarization of the cardiac cycle subsequent to the atrial depolarization, wherein the ventricular depolarization is associated with and precedes the ventricular refractory period, wherein delivering the signal to the supraventricular portion of the heart comprises delivering the signal to the supraventricular portion of the heart subsequent to detection of the ventricular depolarization.

4. The method of claim 3, wherein delivering the pacing signal comprises delivering the pacing signal at a pacing rate, wherein the pacing rate is selected based on a desired ventricular rate.

5. The method of claim 4, wherein delivering the signal to the supraventricular portion of the heart of the patient subsequent to the atrial refractory period and during the ventricular refractory period comprises delivering the signal at a determined time within the cardiac cycle.

6. The method of claim 5, wherein the determined time comprises an interval from at least one of the atrial pacing signal or the atrial depolarization.

7. The method of claim 5, wherein the determined time comprises an interval from the ventricular depolarization.

8. The method of claim 5, wherein the determined time comprises an interval that is determined based on a measured refractory period.

9. The method of claim 5, wherein delivering the signal at a determined time within the cardiac cycle comprises: measuring a physiological parameter of the patient; and determining a time within a predetermined window within the cardiac cycle to deliver the signal to the supraventricular portion of the heart based on the measured physiological parameter.

10. The method of claim 9, wherein the parameter comprises at least one of heart rate or blood pressure.

11. The method of claim 4, further comprising:
identifying a target value of a physiological parameter; sensing the physiological parameter; and titrating delivery of at least one of the pacing signal or the signal to the supraventricular portion of the heart to achieve the target value of the physiological parameter.

12. The method of claim 11, wherein the physiological parameter comprises at least one of heart rate or blood pressure.

13. The method of claim 4, wherein delivering the signal to the supraventricular portion of the heart comprises delivering a train of pulses to the supraventricular portion of the heart.

14. A system comprising: a signal generator configured to deliver a pacing signal configured to cause an atrial depolarization to a heart of a patient, wherein the atrial depolarization results in an associated refractory period during a cardiac cycle, and deliver a signal to a supraventricular portion of the heart of the patient subsequent to the atrial refractory period and during a ventricular refractory period of the cardiac cycle; and a processor configured to control the signal generator to deliver the pacing signal and the signal to the supraventricular portion of the heart; and
further comprising a sensing module configured to detect a ventricular depolarization of the cardiac cycle subsequent to the atrial depolarization, wherein the ventricular depolarization is associated with and precedes the ventricular refractory period, and wherein the signal generator delivers the signal to the supraventricular portion of the heart subsequent to detection of the ventricular depolarization.

15. The system of claim 14, further comprising a lead that comprises at least one electrode coupled to the signal generator, wherein the signal generator delivers the signal to the supraventricular portion of the heart via the at least one electrode of the lead.

16. The system of claim 14, wherein the processor controls the signal generator to deliver the pacing signal at a pacing rate, wherein the pacing rate is selected based on a desired ventricular rate.

17. The system of claim 16, wherein the processor controls the signal generator to deliver the signal to the supraventricular portion of the heart of the patient subsequent to the atrial refractory period and during the ventricular refractory period at a determined time within the cardiac cycle.

18. The system of claim 17, wherein the determined time comprises an interval from at least one of the atrial pacing signal or the atrial depolarization.

19. The system of claim 17, wherein the determined time window comprises an interval from the ventricular depolarization.

20. The system of claim 17, further comprising a sensing module that measures a physiological parameter of the patient, and wherein the processor determines a time within a predetermined window within the cardiac cycle to deliver the signal to the supraventricular portion of the heart based on the measured physiological parameter.

21. The system of claim 20, wherein the parameter comprises at least one of heart rate or blood pressure.

22. The system of claim 16, further comprising a sensing module configured to sense a physiological parameter, wherein the processor identifies a target value of the physiological parameter and controls the signal generator to titrate delivery of at least one of the pacing signal and the signal to the supraventricular portion of the heart to achieve the target value of the physiological parameter.

23. The system of claim 22, wherein the physiological parameter comprises at least one of heart rate or blood pressure.

24. The system of claim 16, further comprising an implantable medical device, wherein the implantable medical device comprises the signal generator and the processor.

25. The system of claim 24, wherein the implantable medical device comprises at least one of a pacemaker, cardioverter, or defibrillator.

26. The system of claim 16, wherein the processor controls the signal generator to deliver at least one of the pacing signal or the signal to the supraventricular portion of the heart as a train of pulses.

27. A method comprising: delivering a pacing signal configured to cause an atrial depolarization to a heart of a patient having intact A-V conduction, wherein the atrial depolarization results in an associated refractory period during a cardiac cycle; and delivering a signal to a supraventricular portion of the heart of the patient subsequent to the atrial refractory period and during a ventricular refractory period of the cardiac cycle, wherein delivering the pacing signal comprises delivering the pacing signal at a pacing rate, wherein the pacing rate is selected based on a desired ventricular rate.

28. The method of claim 27, wherein delivering the signal to the supraventricular portion of the heart comprises delivering the signal to at least one of an atrium, a sinoatrial node, or an atrioventricular node of the heart of the patient.

* * * * *